(12) United States Patent
Mondini et al.

(10) Patent No.: US 8,992,930 B2
(45) Date of Patent: Mar. 31, 2015

(54) EXTRACELLULAR IFI16 AS THERAPEUTIC AGENTS

(75) Inventors: Michele Mondini, Ivrea (IT); Silvia Costa, Tollegno (IT); Marisa Gariglio, Poirino (IT); Santo Landolfo, Turin (IT)

(73) Assignee: University of Piemonte Orientale, Vercelli (IT)

( * ) Notice: Subject to any disclaimer, the term of this patent is extended or adjusted under 35 U.S.C. 154(b) by 0 days.

(21) Appl. No.: 13/575,333

(22) PCT Filed: Jan. 28, 2011

(86) PCT No.: PCT/EP2011/051226
§ 371 (c)(1),
(2), (4) Date: Jul. 26, 2012

(87) PCT Pub. No.: WO2011/092294
PCT Pub. Date: Aug. 4, 2011

(65) Prior Publication Data
US 2013/0058956 A1    Mar. 7, 2013

(30) Foreign Application Priority Data
Jan. 28, 2010 (IT) .............................. MI2010A0115

(51) Int. Cl.
A61K 39/395 (2006.01)
A61K 47/00 (2006.01)
A61K 38/00 (2006.01)
C07K 16/24 (2006.01)
A61K 39/00 (2006.01)

(52) U.S. Cl.
CPC ........... *C07K 16/24* (2013.01); *A61K 2039/505* (2013.01)
USPC .................. 424/172.1; 424/130.1; 424/145.1; 514/16.6; 514/18.6

(58) Field of Classification Search
None
See application file for complete search history.

(56) References Cited

U.S. PATENT DOCUMENTS
2011/0300529 A1* 12/2011 Mondini et al. .................. 435/5

FOREIGN PATENT DOCUMENTS
JP  2006071409 A  3/2006
WO 2010066913 A1  6/2010

OTHER PUBLICATIONS

Mondini et al. (2006), Arthritis & Rheumatism, vol. 54, No. 12, pp. 3939-3944.*
Drosera M et al: "Role of soluble and cell surface molecules in pathogenesis of autoimmune skin diseases", Clinincal and Experimental Rheumatology, Pacina, Pisa, IT, vol. 24, No. 1 Suppl 40, Jan. 1, 2006, pp. S7-S13.
Gariglio M et al: "Immunohistochemical expression analysis of the human interferon-inducible gene IFI16, a member of the HIN200 family, not restricted to hematopoietic cells", Journal of Interferon and Cytokine Research, Mary Ann Liebert, New York, NY, US LNKD-DOI:10.1089/107999002320271413, vol. 22, No. 7, Jul. 1, 2002, pp. 815-821.
Anonymous: "Caratterizzazione molecolare e virologica di pazienti affetti da Epidermodisplasia verruciforme.", [Online] 2007, XP002599134, Dipartimento di Medicina Clinica e Sperimentale. Universita degli Studi del Piemonte Orientale H Amedeo Avogadro Retrieved from the Internet: URL:http://www4.med.unipmn.it/dmcs/ricerca/rs2 007/ViewScheda?chiave_aff=12> [retrieved on Sep. 1, 2010] paragraph risultati ottenuti 4 H.

* cited by examiner

Primary Examiner — Christine J Saoud
Assistant Examiner — Jegatheesan Seharaseyon
(74) Attorney, Agent, or Firm — Rothwell, Figg, Ernst & Manbeck, P.C.

(57) ABSTRACT

The present invention relates to the inhibition of the circulating extracellular form of the interferon inducible protein 16 (extracellular IFI16) for the treatment of diseases, particularly autoimmune and/or inflammatory disorders or infective disorders.

1 Claim, 15 Drawing Sheets

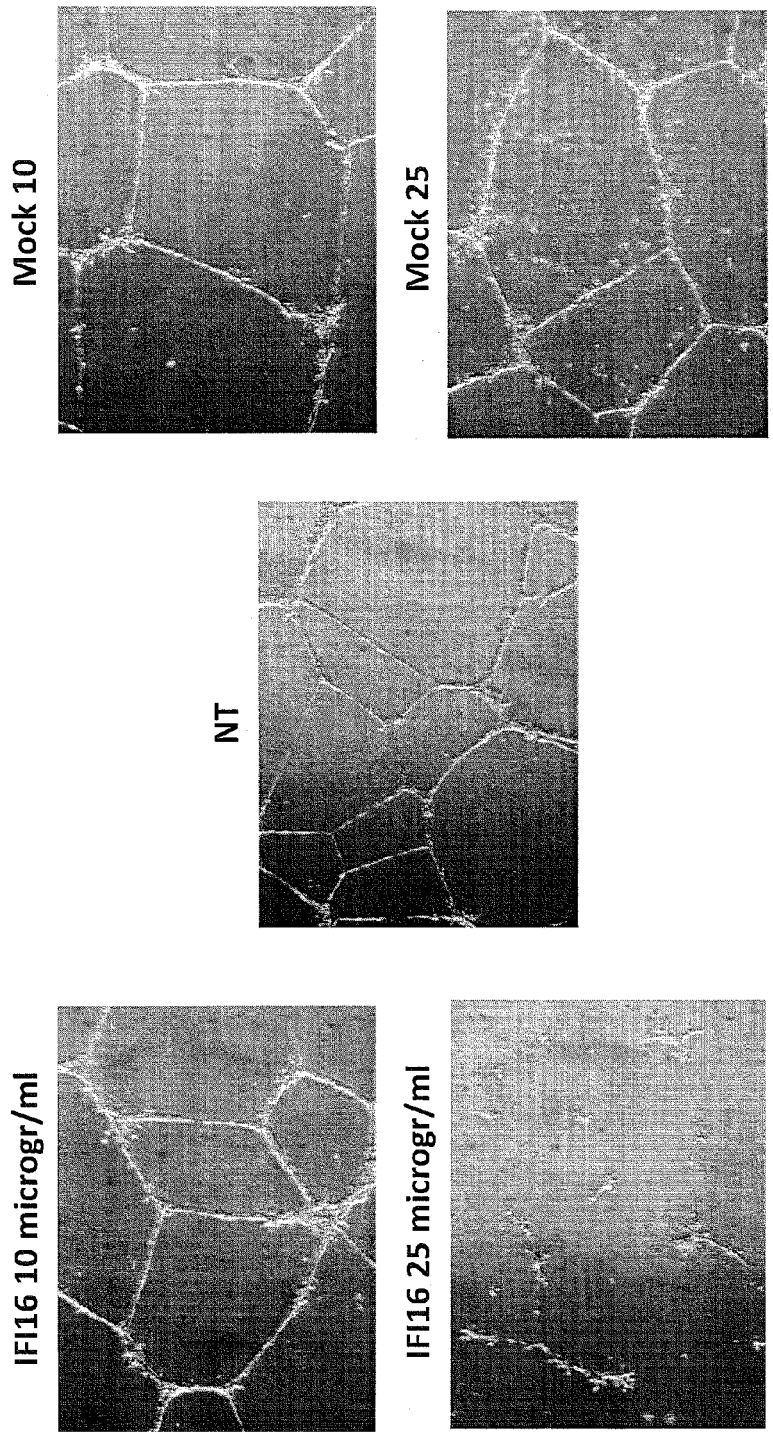

SEQUENCE LISTING

```
<160> NUMBER OF SEQ ID NOS: 3

<210> SEQ ID NO 1
<211> LENGTH: 785
<212> TYPE: PRT
<213> ORGANISM: Homo sapiens
<220> FEATURE:
<221> NAME/KEY: MISC_FEATURE
<222> LOCATION: (1)..(785)
<223> OTHER INFORMATION: human IFI16, isoform a

<400> SEQUENCE: 1
```

```
Met Gly Lys Lys Tyr Lys Asn Ile Val Leu Leu Lys Gly Leu Glu Val
1               5                   10                  15

Ile Asn Asp Tyr His Phe Arg Met Val Lys Ser Leu Leu Ser Asn Asp
            20                  25                  30

Leu Lys Leu Asn Leu Lys Met Arg Glu Glu Tyr Asp Lys Ile Gln Ile
        35                  40                  45

Ala Asp Leu Met Glu Glu Lys Phe Arg Gly Asp Ala Gly Leu Gly Lys
    50                  55                  60

Leu Ile Lys Ile Phe Glu Asp Ile Pro Thr Leu Glu Asp Leu Ala Glu
65                  70                  75                  80

Thr Leu Lys Lys Glu Lys Leu Lys Val Lys Gly Pro Ala Leu Ser Arg
                85                  90                  95

Lys Arg Lys Lys Glu Val Asp Ala Thr Ser Pro Ala Pro Ser Thr Ser
            100                 105                 110

Ser Thr Val Lys Thr Glu Gly Ala Glu Ala Thr Pro Gly Ala Gln Lys
            115                 120                 125

Arg Lys Lys Ser Thr Lys Glu Lys Ala Gly Pro Lys Gly Ser Lys Val
    130                 135                 140

Ser Glu Glu Gln Thr Gln Pro Pro Ser Pro Ala Gly Ala Gly Met Ser
145                 150                 155                 160

Thr Ala Met Gly Arg Ser Pro Ser Pro Lys Thr Ser Leu Ser Ala Pro
                165                 170                 175

Pro Asn Ser Ser Ser Thr Glu Asn Pro Lys Thr Val Ala Lys Cys Gln
            180                 185                 190

Val Thr Pro Arg Arg Asn Val Leu Gln Lys Arg Pro Val Ile Val Lys
            195                 200                 205

Val Leu Ser Thr Thr Lys Pro Phe Glu Tyr Glu Thr Pro Glu Met Glu
    210                 215                 220

Lys Lys Ile Met Phe His Ala Thr Val Ala Thr Gln Thr Gln Phe Phe
225                 230                 235                 240

His Val Lys Val Leu Asn Thr Ser Leu Lys Glu Lys Phe Asn Gly Lys
                245                 250                 255

Lys Ile Ile Ile Ile Ser Asp Tyr Leu Glu Tyr Asp Ser Leu Leu Glu
            260                 265                 270

Val Asn Glu Glu Ser Thr Val Ser Glu Ala Gly Pro Asn Gln Thr Phe
    275                 280                 285

Glu Val Pro Asn Lys Ile Ile Asn Arg Ala Lys Glu Thr Leu Lys Ile
    290                 295                 300

Asp Ile Leu His Lys Gln Ala Ser Gly Asn Ile Val Tyr Gly Val Phe
305                 310                 315                 320

Met Leu His Lys Lys Thr Val Asn Gln Lys Thr Thr Ile Tyr Glu Ile
                325                 330                 335

Gln Asp Asp Arg Gly Lys Met Asp Val Val Gly Thr Gly Gln Cys His
            340                 345                 350

Asn Ile Pro Cys Glu Glu Gly Asp Lys Leu Gln Leu Phe Cys Phe Arg
    355                 360                 365

Leu Arg Lys Lys Asn Gln Met Ser Lys Leu Ile Ser Glu Met His Ser
    370                 375                 380

Phe Ile Gln Ile Lys Lys Lys Thr Asn Pro Arg Asn Asn Asp Pro Lys
385                 390                 395                 400

Ser Met Lys Leu Pro Gln Glu Gln Arg Gln Leu Pro Tyr Pro Ser Glu
                405                 410                 415

Ala Ser Thr Thr Phe Pro Glu Ser His Leu Arg Thr Pro Gln Met Pro
```

```
                    420                 425                 430
Pro Thr Thr Pro Ser Ser Ser Phe Phe Thr Lys Lys Ser Glu Asp Thr
                435                 440                 445

Ile Ser Lys Met Asn Asp Phe Met Arg Met Gln Ile Leu Lys Glu Gly
            450                 455                 460

Ser His Phe Pro Gly Pro Phe Met Thr Ser Ile Gly Pro Ala Glu Ser
465                 470                 475                 480

His Pro His Thr Pro Gln Met Pro Pro Ser Thr Pro Ser Ser Ser Phe
                485                 490                 495

Leu Thr Thr Lys Ser Glu Asp Thr Ile Ser Lys Met Asn Asp Phe Met
                500                 505                 510

Arg Met Gln Ile Leu Lys Glu Gly Ser His Phe Pro Gly Pro Phe Met
                515                 520                 525

Thr Ser Ile Gly Pro Ala Glu Ser His Pro His Thr Pro Gln Met Pro
            530                 535                 540

Pro Ser Thr Pro Ser Ser Ser Phe Leu Thr Thr Leu Lys Pro Arg Leu
545                 550                 555                 560

Lys Thr Glu Pro Glu Glu Val Ser Ile Glu Asp Ser Ala Gln Ser Asp
                565                 570                 575

Leu Lys Glu Val Met Val Leu Asn Ala Thr Glu Ser Phe Val Tyr Glu
                580                 585                 590

Pro Lys Glu Gln Lys Lys Met Phe His Ala Thr Val Ala Thr Glu Asn
                595                 600                 605

Glu Val Phe Arg Val Lys Val Phe Asn Ile Asp Leu Lys Glu Lys Phe
            610                 615                 620

Thr Pro Lys Lys Ile Ile Ala Ile Ala Asn Tyr Val Cys Arg Asn Gly
625                 630                 635                 640

Phe Leu Glu Val Tyr Pro Phe Thr Leu Val Ala Asp Val Asn Ala Asp
                645                 650                 655

Arg Asn Met Glu Ile Pro Lys Gly Leu Ile Arg Ser Ala Ser Val Thr
                660                 665                 670

Pro Lys Ile Asn Gln Leu Cys Ser Gln Thr Lys Gly Ser Phe Val Asn
            675                 680                 685

Gly Val Phe Glu Val His Lys Lys Asn Val Arg Gly Glu Phe Thr Tyr
        690                 695                 700

Tyr Glu Ile Gln Asp Asn Thr Gly Lys Met Glu Val Val His Gly
705                 710                 715                 720

Arg Leu Thr Thr Ile Asn Cys Glu Glu Gly Asp Lys Leu Lys Leu Thr
                725                 730                 735

Cys Phe Glu Leu Ala Pro Lys Ser Gly Asn Thr Gly Glu Leu Arg Ser
                740                 745                 750

Val Ile His Ser His Ile Lys Val Ile Lys Thr Arg Lys Asn Lys Lys
            755                 760                 765

Asp Ile Leu Asn Pro Asp Ser Ser Met Glu Thr Ser Pro Asp Phe Phe
            770                 775                 780

Phe
785

<210> SEQ ID NO 2
<211> LENGTH: 729
<212> TYPE: PRT
<213> ORGANISM: Homo sapiens
<220> FEATURE:
<221> NAME/KEY: MISC_FEATURE
<222> LOCATION: (1)..(729)
```

<223> OTHER INFORMATION: human IFI16, isoform b

<400> SEQUENCE: 2

```
Met Gly Lys Lys Tyr Lys Asn Ile Val Leu Leu Lys Gly Leu Glu Val
1               5                   10                  15

Ile Asn Asp Tyr His Phe Arg Met Val Lys Ser Leu Leu Ser Asn Asp
            20                  25                  30

Leu Lys Leu Asn Leu Lys Met Arg Glu Glu Tyr Asp Lys Ile Gln Ile
            35                  40                  45

Ala Asp Leu Met Glu Glu Lys Phe Arg Gly Asp Ala Gly Leu Gly Lys
        50                  55                  60

Leu Ile Lys Ile Phe Glu Asp Ile Pro Thr Leu Glu Asp Leu Ala Glu
65                  70                  75                  80

Thr Leu Lys Lys Glu Lys Leu Lys Val Lys Gly Pro Ala Leu Ser Arg
                85                  90                  95

Lys Arg Lys Lys Glu Val Asp Ala Thr Ser Pro Ala Pro Ser Thr Ser
                100                 105                 110

Ser Thr Val Lys Thr Glu Gly Ala Glu Ala Thr Pro Gly Ala Gln Lys
            115                 120                 125

Arg Lys Lys Ser Thr Lys Glu Lys Ala Gly Pro Lys Gly Ser Lys Val
130                 135                 140

Ser Glu Glu Gln Thr Gln Pro Pro Ser Pro Ala Gly Ala Gly Met Ser
145                 150                 155                 160

Thr Ala Met Gly Arg Ser Pro Ser Pro Lys Thr Ser Leu Ser Ala Pro
                165                 170                 175

Pro Asn Ser Ser Ser Thr Glu Asn Pro Lys Thr Val Ala Lys Cys Gln
                180                 185                 190

Val Thr Pro Arg Arg Asn Val Leu Gln Lys Arg Pro Val Ile Val Lys
            195                 200                 205

Val Leu Ser Thr Thr Lys Pro Phe Glu Tyr Glu Thr Pro Glu Met Glu
210                 215                 220

Lys Lys Ile Met Phe His Ala Thr Val Ala Thr Gln Thr Gln Phe Phe
225                 230                 235                 240

His Val Lys Val Leu Asn Thr Ser Leu Lys Glu Lys Phe Asn Gly Lys
                245                 250                 255

Lys Ile Ile Ile Ile Ser Asp Tyr Leu Glu Tyr Asp Ser Leu Leu Glu
            260                 265                 270

Val Asn Glu Glu Ser Thr Val Ser Glu Ala Gly Pro Asn Gln Thr Phe
        275                 280                 285

Glu Val Pro Asn Lys Ile Ile Asn Arg Ala Lys Glu Thr Leu Lys Ile
        290                 295                 300

Asp Ile Leu His Lys Gln Ala Ser Gly Asn Ile Val Tyr Gly Val Phe
305                 310                 315                 320

Met Leu His Lys Lys Thr Val Asn Gln Lys Thr Thr Ile Tyr Glu Ile
                325                 330                 335

Gln Asp Asp Arg Gly Lys Met Asp Val Val Gly Thr Gly Gln Cys His
            340                 345                 350

Asn Ile Pro Cys Glu Glu Gly Asp Lys Leu Gln Leu Phe Cys Phe Arg
            355                 360                 365

Leu Arg Lys Lys Asn Gln Met Ser Lys Leu Ile Ser Glu Met His Ser
        370                 375                 380

Phe Ile Gln Ile Lys Lys Lys Thr Asn Pro Arg Asn Asn Asp Pro Lys
385                 390                 395                 400
```

-continued

```
Ser Met Lys Leu Pro Gln Glu Gln Arg Gln Leu Pro Tyr Pro Ser Glu
            405                 410                 415

Ala Ser Thr Thr Phe Pro Glu Ser His Leu Arg Thr Pro Gln Met Pro
        420                 425                 430

Pro Thr Thr Pro Ser Ser Ser Phe Phe Thr Lys Lys Ser Glu Asp Thr
            435                 440                 445

Ile Ser Lys Met Asn Asp Phe Met Arg Met Gln Ile Leu Lys Glu Gly
    450                 455                 460

Ser His Phe Pro Gly Pro Phe Met Thr Ser Ile Gly Pro Ala Glu Ser
465                 470                 475                 480

His Pro His Thr Pro Gln Met Pro Pro Ser Thr Pro Ser Ser Ser Phe
                485                 490                 495

Leu Thr Thr Leu Lys Pro Arg Leu Lys Thr Glu Pro Glu Glu Val Ser
            500                 505                 510

Ile Glu Asp Ser Ala Gln Ser Asp Leu Lys Glu Val Met Val Leu Asn
        515                 520                 525

Ala Thr Glu Ser Phe Val Tyr Glu Pro Lys Glu Gln Lys Lys Met Phe
    530                 535                 540

His Ala Thr Val Ala Thr Glu Asn Glu Val Phe Arg Val Lys Val Phe
545                 550                 555                 560

Asn Ile Asp Leu Lys Glu Lys Phe Thr Pro Lys Lys Ile Ile Ala Ile
                565                 570                 575

Ala Asn Tyr Val Cys Arg Asn Gly Phe Leu Glu Val Tyr Pro Phe Thr
            580                 585                 590

Leu Val Ala Asp Val Asn Ala Asp Arg Asn Met Glu Ile Pro Lys Gly
        595                 600                 605

Leu Ile Arg Ser Ala Ser Val Thr Pro Lys Ile Asn Gln Leu Cys Ser
    610                 615                 620

Gln Thr Lys Gly Ser Phe Val Asn Gly Val Phe Glu Val His Lys Lys
625                 630                 635                 640

Asn Val Arg Gly Glu Phe Thr Tyr Tyr Glu Ile Gln Asp Asn Thr Gly
                645                 650                 655

Lys Met Glu Val Val Val His Gly Arg Leu Thr Thr Ile Asn Cys Glu
            660                 665                 670

Glu Gly Asp Lys Leu Lys Leu Thr Cys Phe Glu Leu Ala Pro Lys Ser
        675                 680                 685

Gly Asn Thr Gly Glu Leu Arg Ser Val Ile His Ser His Ile Lys Val
    690                 695                 700

Ile Lys Thr Arg Lys Asn Lys Lys Asp Ile Leu Asn Pro Asp Ser Ser
705                 710                 715                 720

Met Glu Thr Ser Pro Asp Phe Phe
                725

<210> SEQ ID NO 3
<211> LENGTH: 673
<212> TYPE: PRT
<213> ORGANISM: Homo sapiens
<220> FEATURE:
<221> NAME/KEY: MISC_FEATURE
<222> LOCATION: (1)..(673)
<223> OTHER INFORMATION: human IFI16, isoform c

<400> SEQUENCE: 3

Met Gly Lys Lys Tyr Lys Asn Ile Val Leu Leu Lys Gly Leu Glu Val
1               5                   10                  15

Ile Asn Asp Tyr His Phe Arg Met Val Lys Ser Leu Leu Ser Asn Asp
```

-continued

```
                20                  25                  30
Leu Lys Leu Asn Leu Lys Met Arg Glu Glu Tyr Asp Lys Ile Gln Ile
            35                  40                  45

Ala Asp Leu Met Glu Glu Lys Phe Arg Gly Asp Ala Gly Leu Gly Lys
 50                  55                  60

Leu Ile Lys Ile Phe Glu Asp Ile Pro Thr Leu Glu Asp Leu Ala Glu
 65                  70                  75                  80

Thr Leu Lys Lys Glu Lys Leu Lys Val Lys Gly Pro Ala Leu Ser Arg
                85                  90                  95

Lys Arg Lys Lys Glu Val Asp Ala Thr Ser Pro Ala Pro Ser Thr Ser
                100                 105                 110

Ser Thr Val Lys Thr Glu Gly Ala Glu Ala Thr Pro Gly Ala Gln Lys
145             115                 120                 125

Arg Lys Lys Ser Thr Lys Glu Lys Ala Gly Pro Lys Gly Ser Lys Val
                130                 135                 140

Ser Glu Glu Gln Thr Gln Pro Pro Ser Pro Ala Gly Ala Gly Met Ser
145                 150                 155                 160

Thr Ala Met Gly Arg Ser Pro Ser Pro Lys Thr Ser Leu Ser Ala Pro
                165                 170                 175

Pro Asn Ser Ser Ser Thr Glu Asn Pro Lys Thr Val Ala Lys Cys Gln
                180                 185                 190

Val Thr Pro Arg Arg Asn Val Leu Gln Lys Arg Pro Val Ile Val Lys
                195                 200                 205

Val Leu Ser Thr Thr Lys Pro Phe Glu Tyr Glu Thr Pro Glu Met Glu
                210                 215                 220

Lys Lys Ile Met Phe His Ala Thr Val Ala Thr Gln Thr Gln Phe Phe
225                 230                 235                 240

His Val Lys Val Leu Asn Thr Ser Leu Lys Glu Lys Phe Asn Gly Lys
                245                 250                 255

Lys Ile Ile Ile Ile Ser Asp Tyr Leu Glu Tyr Asp Ser Leu Leu Glu
                260                 265                 270

Val Asn Glu Glu Ser Thr Val Ser Glu Ala Gly Pro Asn Gln Thr Phe
                275                 280                 285

Glu Val Pro Asn Lys Ile Ile Asn Arg Ala Lys Glu Thr Leu Lys Ile
                290                 295                 300

Asp Ile Leu His Lys Gln Ala Ser Gly Asn Ile Val Tyr Gly Val Phe
305                 310                 315                 320

Met Leu His Lys Lys Thr Val Asn Gln Lys Thr Thr Ile Tyr Glu Ile
                325                 330                 335

Gln Asp Asp Arg Gly Lys Met Asp Val Val Gly Thr Gly Gln Cys His
                340                 345                 350

Asn Ile Pro Cys Glu Glu Gly Asp Lys Leu Gln Leu Phe Cys Phe Arg
                355                 360                 365

Leu Arg Lys Lys Asn Gln Met Ser Lys Leu Ile Ser Glu Met His Ser
                370                 375                 380

Phe Ile Gln Ile Lys Lys Lys Thr Asn Pro Arg Asn Asn Asp Pro Lys
385                 390                 395                 400

Ser Met Lys Leu Pro Gln Glu Gln Arg Gln Leu Pro Tyr Pro Ser Glu
                405                 410                 415

Ala Ser Thr Thr Phe Pro Glu Ser His Leu Arg Thr Pro Gln Met Pro
                420                 425                 430

Pro Thr Thr Pro Ser Ser Ser Phe Phe Thr Lys Leu Lys Pro Arg Leu
                435                 440                 445
```

```
Lys Thr Glu Pro Glu Val Ser Ile Glu Asp Ser Ala Gln Ser Asp
    450             455             460

Leu Lys Glu Val Met Val Leu Asn Ala Thr Glu Ser Phe Val Tyr Glu
465             470             475             480

Pro Lys Glu Gln Lys Lys Met Phe His Ala Thr Val Ala Thr Glu Asn
            485             490             495

Glu Val Phe Arg Val Lys Val Phe Asn Ile Asp Leu Lys Glu Lys Phe
            500             505             510

Thr Pro Lys Lys Ile Ile Ala Ile Ala Asn Tyr Val Cys Arg Asn Gly
            515             520             525

Phe Leu Glu Val Tyr Pro Phe Thr Leu Val Ala Asp Val Asn Ala Asp
    530             535             540

Arg Asn Met Glu Ile Pro Lys Gly Leu Ile Arg Ser Ala Ser Val Thr
545             550             555             560

Pro Lys Ile Asn Gln Leu Cys Ser Gln Thr Lys Gly Ser Phe Val Asn
            565             570             575

Gly Val Phe Glu Val His Lys Lys Asn Val Arg Gly Glu Phe Thr Tyr
            580             585             590

Tyr Glu Ile Gln Asp Asn Thr Gly Lys Met Glu Val Val His Gly
    595             600             605

Arg Leu Thr Thr Ile Asn Cys Glu Glu Gly Asp Lys Leu Lys Leu Thr
    610             615             620

Cys Phe Glu Leu Ala Pro Lys Ser Gly Asn Thr Gly Glu Leu Arg Ser
625             630             635             640

Val Ile His Ser His Ile Lys Val Ile Lys Thr Arg Lys Asn Lys Lys
            645             650             655

Asp Ile Leu Asn Pro Asp Ser Ser Met Glu Thr Ser Pro Asp Phe Phe
            660             665             670

Phe
```

EXTRACELLULAR IFI16 AS THERAPEUTIC AGENTS

CROSS REFERENCE TO RELATED APPLICATION

Figure 1:
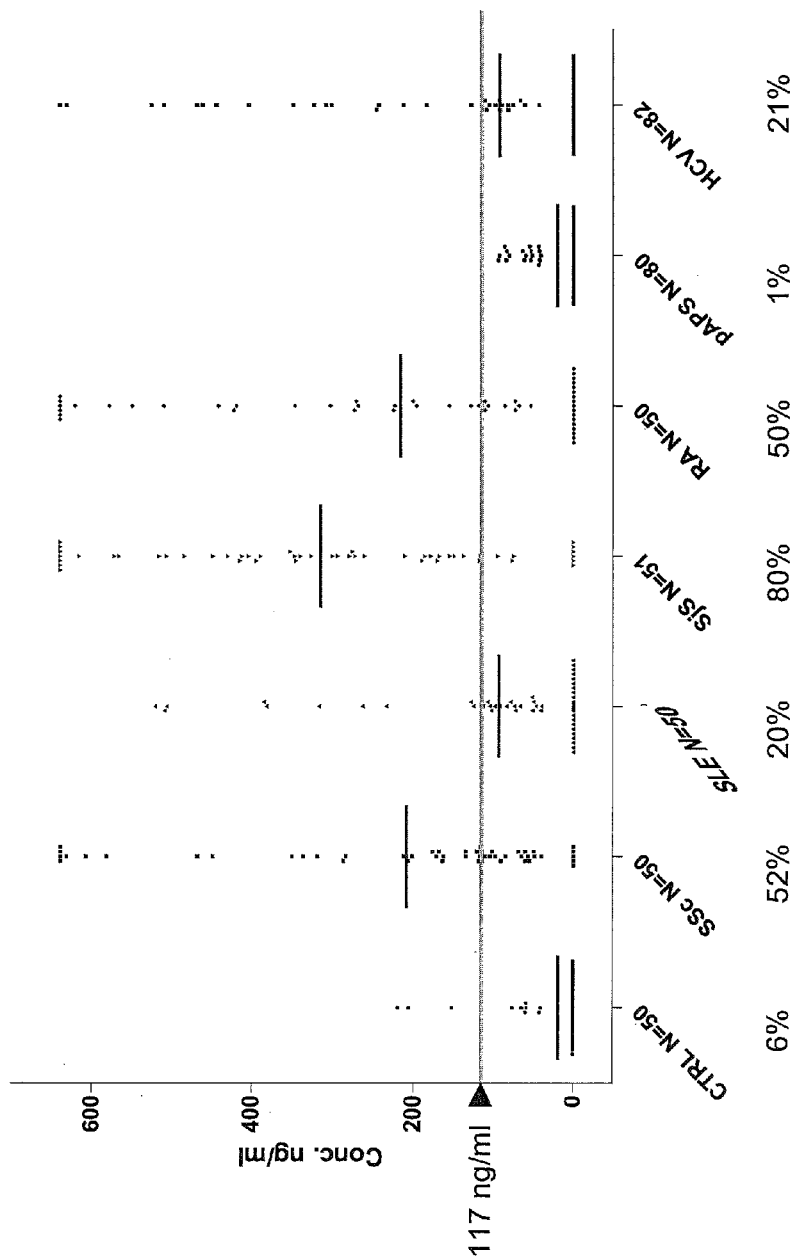

This application is a 35 U.S.C. 371 National Phase Entry Application from PCT/EP2011/051226, filed Jan. 28, 2011, which claims the benefit of Italian Patent Application No. MI 2010 A 000 115 filed on Jan. 28, 2010, the disclosures of which are incorporated herein in their entirety by reference.

REFERENCE TO A SEQUENCE LISTING

The present application includes a Sequence Listing filed in electronic format. The Sequence Listing is entitled "2923-1167_ST25.txt" created on Oct. 31, 2012, and is 19,000 bytes in size. The information in the electronic format of the Sequence Listing is part of the present application and is incorporated herein by reference in its entirety.

The present invention relates to the inhibition of the circulating extracellular form of the interferon inducible protein 16 (extracellular IFI16) for the treatment of diseases, particularly autoimmune and/or inflammatory disorders or infective disorders.

Interferons (IFNs) are important regulators of viral replication, cell growth, immuno-modulation and inflammation (1,2). Moreover, it is now well accepted that IFNs play a critical role in the pathogenesis and perpetuation of specific autoimmune diseases, including Systemic Lupus Erythematosus (SLE), Systemic Sclerosis (SSc), autoimmune thyroid disease and type 1 diabetes (3).

The interferon-inducible p200 family of proteins (Ifi200 in the mice, HIN200 in the humans) is among the numerous gene products induced by IFNs (4-6). Recently, the Pyrin domain, commonly found among cell death-associated proteins such as Pyrin, ASC, and zebrafish caspase and also referred to as the PAAD/DAPIN domain (7, 8), has been found in the N-terminus of most Ifi200/HIN200 proteins, suggesting a role of these proteins in inflammation and apoptosis (9, 10).

The interferon-inducible 16 (IFI16) gene (also known as PYHIN2, IFNGIP1, MGC9466), a member of the HIN200 family (4-6), was originally identified as a target of interferons (IFN-$\alpha/\beta$ and -$\gamma$). Recently however, it has become clear that oxidative stress, cell density, and various proinflammatory cytokines also trigger IFI16 expression (11, 12). IFI16 expression is seen in vascular endothelial cells from blood and lymph vessels in addition to hematopoietic cells, suggesting a possible link to angiogenesis and inflammation (13, 14).

IFI16 protein, as the other members of HIN-200 family, displays a Pyrin domain at its N terminus, suggesting a role for this protein in the apoptotic pathway by regulating the activity of certain transcription factors in the nucleus that are involved in the commitment to cell death (15). For instance, IFI16 binds directly p53 at nuclear level and enhances its DNA-binding activity.

Gene array analysis of human vascular endothelial cells overexpressing IFI16, revealed an increased expression of genes involved in the regulation of the immune system (16). IFI16 triggered the expression of adhesion molecules such as intercellular adhesion molecule-1 (ICAM-1) and E-selectin or chemokines such as IL-8 and monocyte chemoattractant protein-1 (MCP-1). Treatment of cells with short hairpin RNA targeting IFI16 significantly inhibited ICAM-1 induction by IFN-$\gamma$, demonstrating that IFI16 is involved in proinflammatory gene stimulation by IFN-$\gamma$. Moreover, functional analysis of the ICAM-1 promoter demonstrated that NF-kB is the main mediator of IFI16-driven gene induction (16).

Additionally, it has been demonstrated that IFI16 is a target of autoantibodies. Anti-IFI16 autoantibody titers are significantly elevated in patients with autoimmune diseases such as systemic sclerosis (SSc), systemic lupus erythematosus (SLE), and Sjogren's syndrome (SjS), when compared with controls (17).

Nevertheless, all the biological activities of IFI16 reported in the literature, as well as their possible links to human pathologies, were assigned to (and limited to) an intracellular (in particular nuclear) protein, which was the unique localization previously described for IFI16. Indeed, all the in vitro studies were performed by overexpressing or downregulating IFI16 in different cell models, and the modulation of IFI16 was always monitored intracellularly (i.e. by performing cell extract or by analyzing the presence of IFI16 directly inside the cells, for instance by immunofluorescence techniques).

PCT/EP2009/067128 describes the presence of detectable amounts of extracellular form of IFI16 in the sera of patients affected by pathological conditions, in particular by autoimmune, inflammatory and/or infective diseases. By an IFI16 sandwich ELISA, significantly high levels of circulating IFI16 have been found in patients affected by SSc, SLE, SjS and Rheumatoid Arthritis, as well as in patients suffering from Hepatitis C Virus (HCV) infection, when compared with healthy patients as control.

The present inventors now have found that the extracellular form of IFI16 is a therapeutic target and, in particular, that the modulation, in particular the inhibition of extracellular IFI16 protein activity leads to a prevention, repression and/or alleviation of pathological conditions, in particular associated with autoimmune, inflammatory and/or infectious diseases.

In the present invention, it is shown for the first time that extracellular IFI16 can exert biological effects. In particular, the authors carried out experiments by administration of extracellular IFI16 to human primary cells and assessed whether the biological parameters of the cultured cells were influenced.

Administration of extracellular IFI16 was shown to influence the number of live adherent human primary cells. Epithelial and endothelial cell cultures exposed to extracellular IFI16 showed a decrease in the number of live adherent cells, when compared to control cells (Example 2.1 and FIGS. 2a, 2b and 2c). Further it was shown that extracellular IFI16 interferes with cellular migration of target cells. Treatment of cells (for example, primary human keratinocytes (KER) and Human Umbilical Vascular Endothelial Cells (HUVEC)) with the extracellular protein showed limited/reduced migration capabilities (Example 2.2 and FIGS. 3a, 3b, 3c and 4a and 4b). Moreover, the authors of the present invention could prove the effect of extracellular IFI16 on vascular development (angiogenesis), whereby specific assays show that tubulogenesis by HUVEC is severely limited when cells are exposed to extracellular IFI16 (Example 2.4 and FIGS. 6a and 6b).

Vascular endothelial cell damage is a pathological condition which is frequently found in various autoimmune diseases, e.g. systemic lupus erythematosus and systemic sclerosis, as well as in infectious diseases (Youinou, Immunobiology 210 (2005, 789-797). Another important target in the autoimmune disorders is represented by the skin (Abraham et al., Rheumatology 2009, 48:iii3-iii7). Indeed, both endothelial and epithelial cells are often involved in the pathogenetic processes triggered either by autoimmunity or infections.

The presence of significant amounts of extracellular IFI16 in pathological conditions together with the above reported experimental results demonstrate that the extracellular IFI16 protein may be a target of a therapeutic intervention. Thus, inhibition of extracellular IFI16 protein may be regarded as novel therapeutic approach in medicine, particularly in the treatment of autoimmune, inflammatory, and/or infectious diseases. More particularly, inhibition of the extracellular form of IFI16 may be suitable for the prevention, treatment and/or alleviation of cutaneous lesions involved in autoimmune and/or inflammatory and/or infectious diseases.

Thus, a first aspect of the present invention refers to an inhibiting agent of the circulating extracellular form of the interferon-inducible protein 16 (extracellular IFI16) for use as a medicament. Particularly, the inhibiting agent may be used for the prevention, treatment and/or alleviation of autoimmune and/or inflammatory diseases. More particularly, the extracellular IFI16 inhibiting agent may be used for the treatment of disorders selected from Systemic Sclerosis (SSc), Systemic Lupus Erytemathosus (SLE), Sjogren's Syndrome (SjS) and rheumatoid arthritis (RA). Further examples of autoimmune diseases and/or inflammatory diseases include autoimmune hepatitis, primary biliary cirrhosis, antiphosholipid syndrome, autoimmune thyroid disease and type 1 diabetes. In a very preferred embodiment of the present invention, the inhibiting agents may be used for the prevention, treatment and/or alleviation of cutaneous lesions which are involved in autoimmune and/or inflammatory diseases, e.g. as described above.

The inhibiting agent of extracellular IFI16 may also be used for the prevention, treatment and/or alleviation of infectious diseases. The infectious disease may be selected from viral, bacterial and/or parasitic infections. Particularly, the infectious disease is a viral infection by e.g. hepatitis C virus (HCV). Further examples of infectious diseases include viral infection by hepatitis B virus (HBV), or Human Immunodeficiency Virus (HIV).

The inhibiting agent of the present invention is selected from inhibitors of the circulating extracellular form of IFI16. Thus, the inhibiting agent of the invention preferably acts on the protein level by binding to the circulating extracellular IFI16 and thereby influencing, e.g. reducing, protein activity. In a preferred embodiment, the inhibiting agent binds to IFI16 in the extracellular environment. The inhibiting agents of the invention preferably modulate, i.e. reduce, the biological activity of mammalian circulating extracellular IFI16, e.g. bovine, human, horse, cat, dog, rabbit, sheep, mouse, hamster, rat and/or pig, very preferably mouse and/or human extracellular IFI16. The human IFI16 disclosed in the present invention as a therapeutic target comprises at least one naturally occurring isoform of IFI16, in particular the isoform a (UniProtKB Accession No. Q16666-1), the isoform b (UniProtKB Accession No. Q16666-2) and the isoform c (UniProtKB Accession No. Q16666-3), fragments or variants thereof. The human IFI16 isoforms may specifically have the sequences SEQ ID NO: 1 (isoform a), SEQ ID NO: 2 (isoform b) and SEQ ID NO: 3 (isoform c).

For example, the inhibitor may be selected from an antibody specific for IFI16 or an antigen-binding fragment thereof, an aptamer directed against IFI16 or a mutated form of IFI16.

Preferably, the IFI16 inhibitor is an antibody specific for extracellular IFI16 or an antigen-binding fragment thereof. The antibody may be selected from a polyclonal antibody, a monoclonal antibody, a chimeric antibody, a humanized antibody, a human antibody, a recombinant antibody or an antigen-binding fragment thereof.

For the production of antibodies, a host animal, e.g. a mouse or a rabbit, may be immunised with an IFI16 antigen, optionally together with an adjuvant to increase the immunological response. A monoclonal antibody may be prepared by using known techniques including, but not limited to, the hybridoma technique developed by Köhler and Milstein. Chimeric antibodies may be obtained from monoclonal antibodies by replacing non-human constant regions by appropriate human constant regions. Humanized antibodies may be obtained by replacing non-human framework regions in the variable antibody domains by appropriate human sequences. Human antibodies may be obtained from host animals, e.g. mice, comprising a xenogenic human immune system. Recombinant antibodies may be obtained by phage display and affinity maturation of given antibody sequences. Recombinant antibodies may be single-chain antibodies, bispecific antibodies, etc.

Antibody fragments which contain at least one binding site for extracellular IFI16 may be selected from Fab fragments, Fab'-fragments, F(ab')$_2$ fragments or single-chain Fv fragments.

In a very preferred embodiment of the invention the antibody or the antigen-binding fragment thereof specifically binds to mammalian circulating extracellular IFI16, particularly to human extracellular IFI16, including IFI16 isoform a, isoform b and/or isoform c. Specific embodiments of preferred anti-IFI16 antibodies are antibodies generated against an IFI16 fragment corresponding to amino acids 478-729 of the b isoform of IFI16.

In this preferred embodiment, the present inventors found that anti-IFI16 antibodies can be used as inhibiting agents to revert the effects of extracellular IFI16. In particular, anti-IFI16 antibodies have been used to inhibit the activity of extracellular IFI16 on the viability of adherent HUVEC (Example 3.1 and 3.3 and FIGS. 7 and 9). Further, anti-IFI16 antibodies have been shown to restore the wound healing capabilities limited by extracellular IFI16 (Example 3.2). Indeed in a in vitro wound healing assay, the use of anti-IFI16 restored the wound closure capability of KER treated with extracellular IFI16 (FIG. 8).

Aptamers directed against extracellular IFI16 may be obtained by affinity selection of nucleic acid and/or peptidic sequences according to known protocols.

A mutated form of IFI16 may be selected from IFI16 molecules which have been modified by mutation, e.g. substitution, deletion and/or addition of amino acid residues. Preferred mutated IFI16 molecules exhibit a partial or complete inhibitory effect on at least one IFI16 activity as shown in the examples of the present invention. Examples of such mutated IFI16 molecules are truncated forms of IFI16, e.g. comprising deletion of at least 20, 50 or 100 amino acids of a naturally occurring IFI16 molecule, e.g. as described above.

The inhibiting agent of extracellular IFI16 may administered as a monotherapy or in combination with an additional therapy, or with at least one further additional therapeutic active agent, e.g. an anti-autoimmune agent and/or an anti-inflammatory agent. Examples of further autoimmune agents may include, e.g. abatacept, adalimumab, anakinra, azathioprine, chloroquine, cyclophosphamide, cyclosporin, D-penicillamine, etanercept, golimumab, auranofin, infliximab, leflunomide, methotrexate, minocycline, rituximab, sulfasalazine, tocilizumab, glucocorticoids or non-steroidal anti-inflammatory drugs (NSAIDs such as paracetamol and ibuprofen). Examples of further anti-inflammatory agents may include, e.g. prostaglandins, glucocorticoids or NSAIDs.

For the treatment of infectious diseases, the inhibiting agent of extracellular IFI16 may be administered alone or in combination with an additional therapy directed against the infectious agent, particularly with at least one further antipathogenic agent, preferably a further antiviral agent. The further antiviral agent may be selected from a protease inhibitor, a polymerase inhibitor, an integrase inhibitor, an entry inhibitor, an assembly/secretion inhibitor, a translation inhibitor, an immunostimulant or any combination thereof.

A further aspect of the invention is a pharmaceutical composition which comprises as an active agent at least one inhibiting agent of extracellular IFI16 as described above together with a pharmaceutically acceptable carrier, diluent and/or adjuvant. The pharmaceutical composition may be formulated as e.g. tablets, pills, capsules, liquids, gels, syrups, slurries, suspensions, etc. Depending on the specific disorder to be treated the composition may be administered systematically or locally. Suitable routes may include, e.g. oral, rectal, transmucosal, intestinal, intranasal, intraocular or pulmonal administration or parenteral delivery including intramuscular, subcutaneous, intrathecal, intravenous or intraperitonal injection or infusion.

The pharmaceutical composition comprises the active agent in an effective dose sufficient to achieve its intended purpose. The determination of an effective dose can be carried out by the skilled person. For example, the effective dose may be estimated from cell culture assays and/or in animal models. Usual dosage for administration in human medicine may range from e.g. 0.01-2000 mg/day, commonly from 0.1-1000 mg/day and typically from 1-500 mg/day.

A further aspect of the present invention is directed to a pharmaceutical composition or a kit which comprises at least one inhibiting agent as described above in combination with at least one further anti-autoimmune agent and/or at least one further anti-inflammatory agent and/or with at least one further antiviral agent as described above.

The pharmaceutical composition is preferably for use in medicine, e.g. in human or veterinary medicine. Thus, it is provided a method for treating a subject suffering from an autoimmune and/or inflammatory disease and/or an infectious disease comprising administering to a subject in need thereof a pharmaceutically effective amount of an inhibiting agent of extracellular IFI16 or a pharmaceutical composition comprising at least one inhibiting agent of extracellular IFI16 as an active ingredient. The autoimmune and/or inflammatory disease is preferably selected from Systemic Sclerosis, Systemic Lupus Erytemathosus, Sjogren's Syndrome and Rheumatoid Arthritis. The infectious disease is preferably a HCV infection.

Finally, the present invention also refers to a method of screening for an anti-autoimmune agent and/or an anti-inflammatory agent or an anti-pathogen agent, e.g. antiviral agent, comprising the steps of determining if a test compound is capable of modulating, preferably inhibiting, the biological activity of extracellular IFI16. The screening method may, for example, comprise the steps of:
(a) providing an extracellular IFI16,
(b) contacting a test compound with said extracellular IFI16 of (a),
(c) determining the amount of IFI16 through binding of the test compound to extracellular IFI16 and/or determining the activity of extracellular IFI16 in the presence of the test compound compared to a control, e.g. in the absence of a test compound, and finally
(d) selecting a compound which modulates, preferably inhibits, the biological activity of extracellular IFI16 protein.

The screening method of the present invention may comprise a cellular screening assay or/and a molecular screening assay. Hence, the screening may be carried out in a cell-free or cellular system. For cellular screening methods, the use of recombinant cells or non-human organisms capable of expressing and/or releasing extracellular IFI16 is preferred. In the screening method of the present invention, the extracellular IFI16 may also be provided in an isolated form, including e.g. essentially pure and crude preparations or formulations of IFI16 protein.

The test compound may be selected from polypeptides, e.g. antibodies or antibody fragments, aptamers, peptidic compounds or non-peptidic low molecular weight organic molecules (e.g. having a molecular weight of up to 2000 Da). A test compound which is identified as an inhibiting agent of extracellular IFI16 protein in a screening method as described above may be a suitable candidate agent for the treatment of autoimmune and/or inflammatory diseases and/or infectious diseases.

Further, the present invention is explained in more detail by the following figures and examples.

FIGURES LEGENDS

FIG. 1: Measuring circulating IFI16 in autoimmune patients and healthy subjects using an IFI16 ELISA.

The concentration of circulating IFI16 in sera was determined by means of ELISA in patients suffering from Systemic Sclerosis (SSc, n=50), Systemic Lupus Erytemathosus (SLE, n=50), Sjogren's Syndrome (SjS n=51), RA (50), anti-phospholipid syndrome (pAPS, 80) and patients with hepatitis C virus infection (HCV, 82) and in healthy subjects (CTRL, 50).

ELISA microtitre plates were coated with a polyclonal rabbit-anti-IFI16 antibody. Subsequently, the plates were washed and free binding sites were saturated with PBS/0.05% Tween-20/3% BSA (PBS-TB) at room temperature for 1 hour. After washing, an incubation followed (1 h, room temperature) with 5 µl of different sera samples in a final volume of 100 µl of PBS/0.05% Tween-20/1% BSA (PBS-TD). Purified 6His-IFI16 protein, diluted in 5% FBS in PBS-TD was used as standard. BSA served as negative control. The samples were washed and in each case monoclonal mouse anti-IFI16 antibody was added and incubated for 1 h at room temperature. After washing, an incubation followed (1 h, room temperature) with HRP-conjugated anti-mouse antibody diluted in PBS-TD. After washing, the IFI16 protein/antibody complex was visualised by incubation with tetramethylbenzidine (TMB) and stopped with Stop Solution. The absorption was measured at 450 nm in the micro plate reader. The determination of the concentration was carried out using a standard curve for which increasing concentrations of purified 6His-IFI16 were used. The linearity of the measurement ranged from 20 to 640 ng/ml IFI16 in the sera. Sera with a concentration outside the linearity range (<20 ng/ml or >640 ng/ml) are plotted as having 0.1 ng/ml or 640 ng/ml respectively. Red horizontal lines (single grey horizontal lines) represent the mean IFI16 concentrations for each patient group.

A cut-off value for IFI16 positivity was set at 95° percentile of control population (117 ng/ml), and is represented by a green horizontal line (light grey continuous horizontal line). The numbers below the X axis represent the percentage of patients with IFI16 serum concentrations higher than the cut-off level in each group. The IFI16 serum protein was detectable at level higher than the cut-off in a fraction of SSc, SLE, SjS, RA and HCV patients sera ranging from 20% to 80%, while only in 6% the healthy subjects. Only 1% of patients suffering from pAPS were positive for circulating IFI16.

Figure 2A:
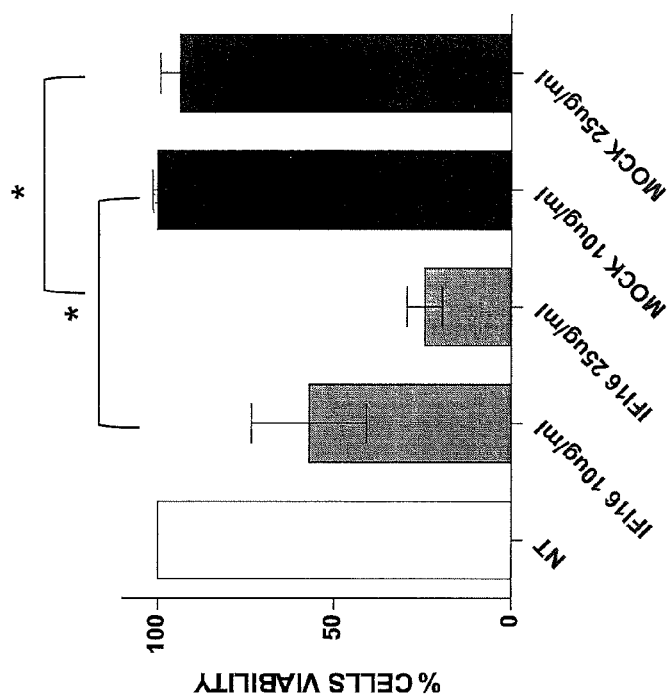
Figure 2A:
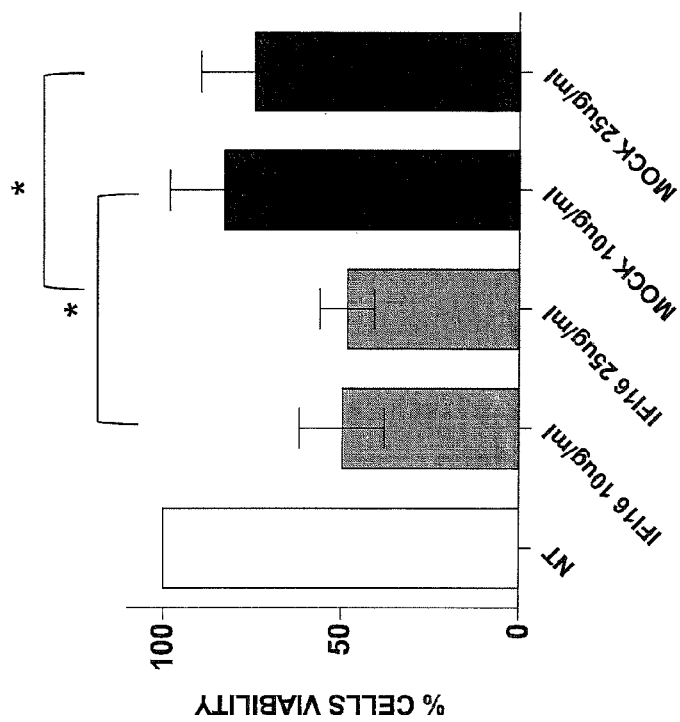

FIG. 2a: Viability analysis of adherent human epithelial and endothelial cells treated with IFI16.

Extracellular IFI16 affects the amount of viable adherent human epithelial (A) and endothelial (B) cells.

Panel A: human primary keratinocytes (KER) were cultured in serum-free medium (Epilife, Cascade Biologics, USA), containing growth factors. 5000-10000 cells were seeded in a 96 well culture plate and after 24 hours treated with different doses (10 or 25 µg/ml) of recombinant IFI16 protein (IFI16), produced in E. coli encoding the full-length b isoform of human IFI16 and then purified by 3 sequential chromatographic steps to obtain high purity endotoxin-free protein. As negative controls, cells were treated with the same volumes of vehicle (Mock) used for each IFI16 dose or left untreated (NT). After 48 hours, the cells were treated with 3-(4,5-Dimethylthiazol-2-yl)-2,5-diphenyltetrazolium bromide (MTT) for 3 hours at 37° C. and then the medium was aspirated and the MTT crystals were dissolved with DMSO. The absorbance, proportional to the amount of viable adherent cells, was read at 570 nm. *$p<0.01$ by one-way ANOVA and Bonferroni's post-test.

Panel B: primary human umbilical vein embryo cells (HUVEC) were cultured in complete endothelial growth medium (EGM-2, Clonetics, USA) containing 2% FBS. 3000 cells were seeded in a 96 well culture plate and then processed as in panel A. $p<0.01$ by one-way ANOVA and Bonferroni's post-test.

Figure 2B:
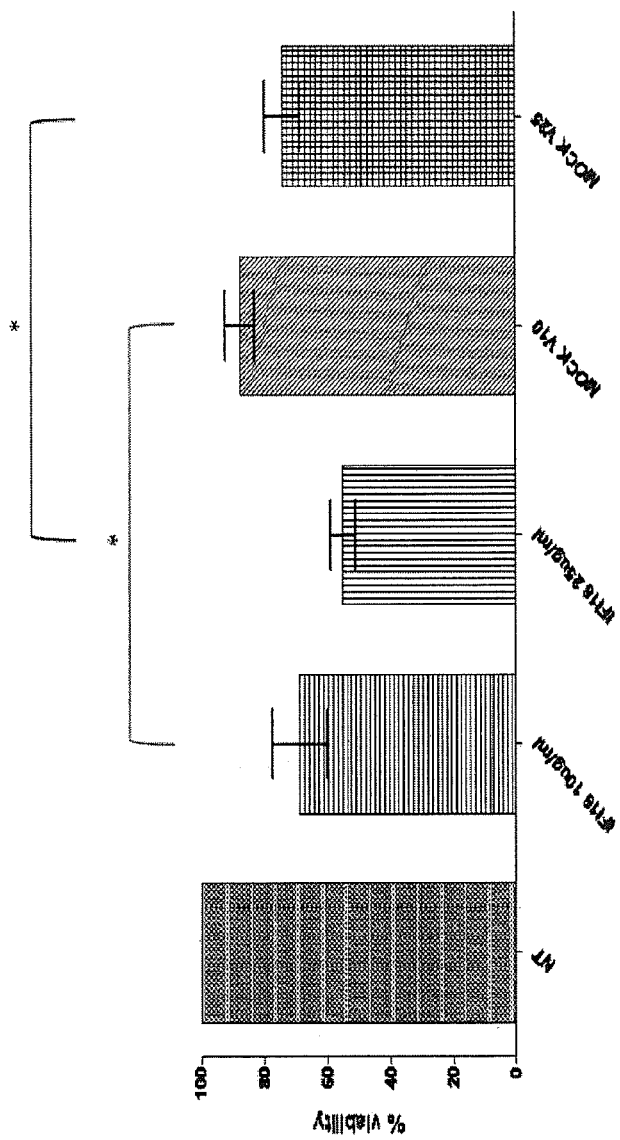

FIG. 2b: Viability analysis of adherent human epithelial cells treated with different doses of recombinant IFI16 protein, Mock treated or left untreated for 48 hours. Values represent the mean±SEM of seven independent experiments (* $p<0.05$, one-way ANOVA followed by Bonferroni's Multiple Comparison Test).

Primary human keratinocytes (KER) were cultured in serum-free medium (Epilife, Cascade Biologics, USA), containing growth factors. $1\times10^4$ cells were seeded in a 96 well culture plate and after 24 hours treated with different doses (10 or 25 µg/ml) of recombinant IFI16 protein (IFI16) (produced by Notopharm srl). As negative controls, cells were treated with the same volumes of vehicle (Mock) (produced by Notopharm srl) used for each IFI16 dose or left untreated (NT). After 48 hours incubation, cells were treated with 3-(4,5-Dimethylthiazol-2-yl)-2,5-diphenyltetrazolium bromide (MTT) for 3 hours at 37° C., then the medium was discarded and the MTT crystals were dissolved with DMSO. The absorbance, proportional to the amount of viable adherent cells, was read at 570 nm with a spectrophotometer.

Figure 2C:
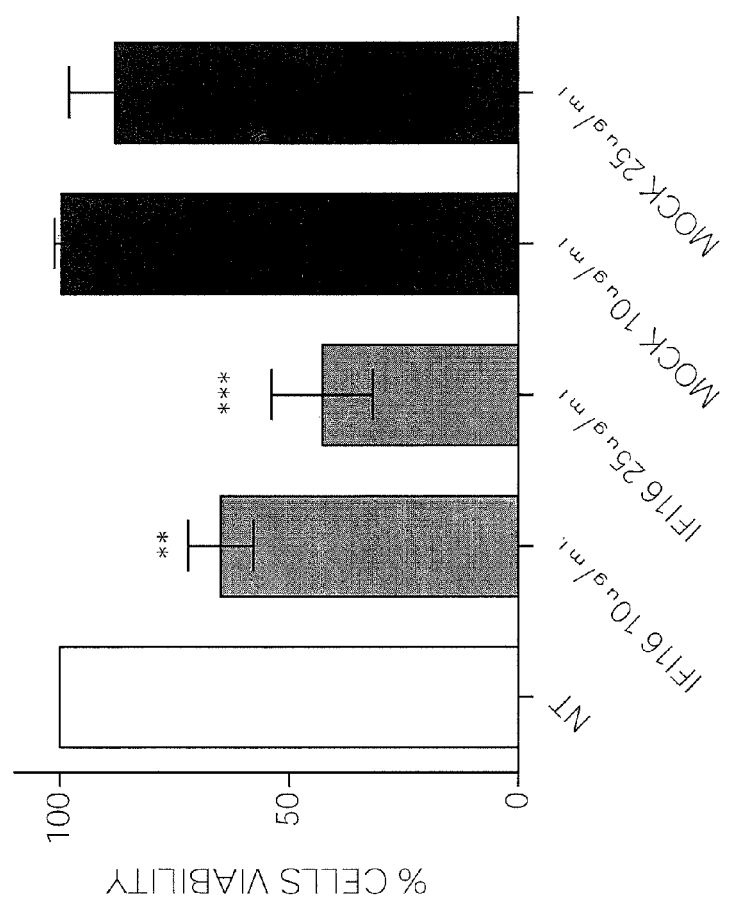

FIG. 2c: Viability analysis of HUVEC cells treated with different doses of recombinant IFI16 protein, Mock treated or left untreated for 48 hours. Values represent the mean±SEM of 4 independent experiments ( $P<0.01$, * $P<0.001$, one-way ANOVA followed by Bonferroni's Multiple Comparison Test).

$3\times10^3$ HUVEC cells were seeded in a 96 well culture plate and after 24 hours treated with different doses (10 or 25 µg/ml) of recombinant IFI16 protein (IFI16) (produced by Notopharm srl). As negative controls, cells were treated with the same volumes of vehicle (Mock) (produced by Notopharm srl) or left untreated (NT). After 48 hours incubation, cells were treated with 3-(4,5-Dimethylthiazol-2-yl)-2,5-diphenyltetrazolium bromide (MTT) for 2 hours at 37° C., then the medium was discarded and the MTT crystals were dissolved with DMSO. The absorbance, proportional to the amount of viable adherent cells, was read at 570 nm with a spectrophotometer.

Figure 3A:
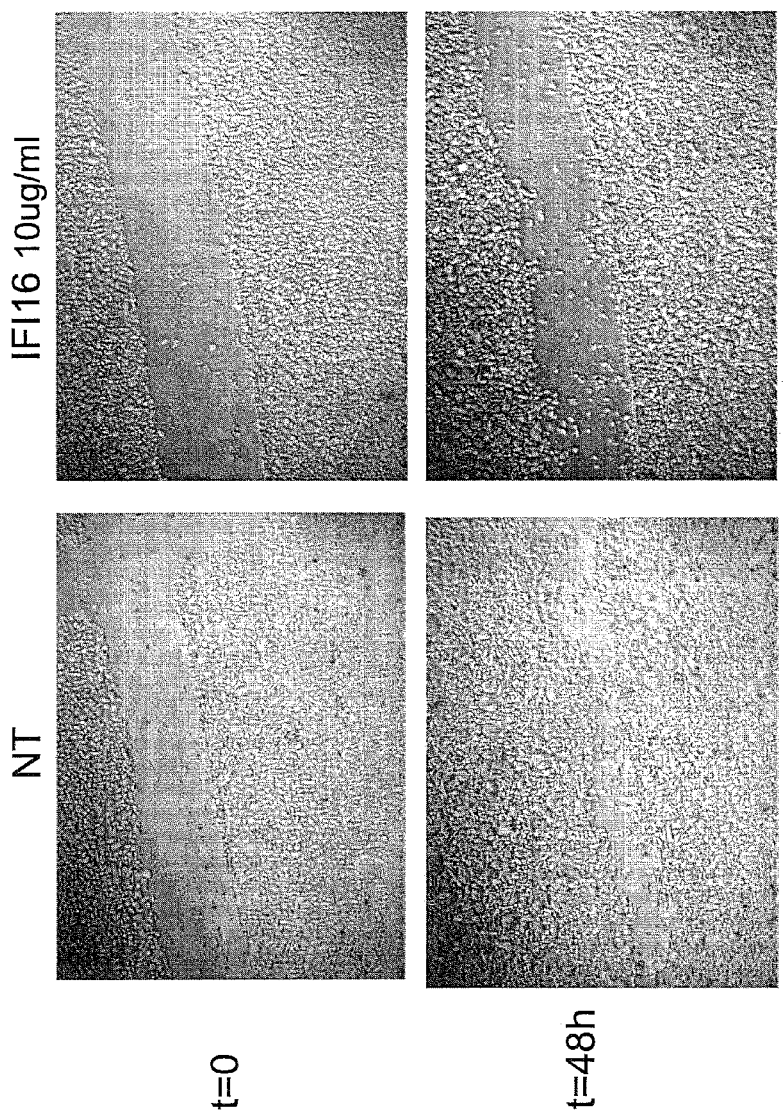

FIG. 3a: In vitro scratch assay analysis of adherent human epithelial cells treated with IFI16.

Extracellular IFI16 impairs human keratinocytes migration. The cells were seeded to a density of $5\times10^5$ in a 6 well culture plate and grown to confluence for 24 hours. Then the medium was removed and cells were washed with PBS. Three artificial wounds (one vertical and two horizontals) were carefully created using a pipette tip to scratch the confluent cell monolayer to make a cell-free area. The cells were washed twice with PBS to remove scratched debris and plates were photographed using a Leica inverted microscope (0 hours). Epilife complete medium, containing or not 10 µg/ml of IFI16, was then added and cells were incubated for 48 hours, when pictures of the same areas were taken.

Figure 3B:
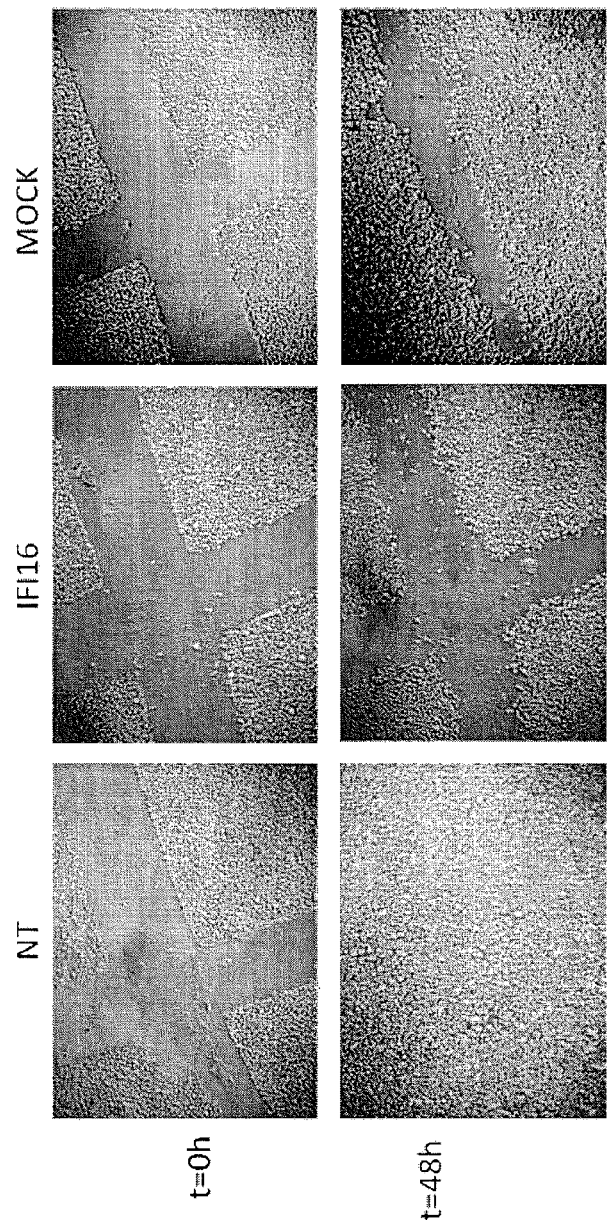
Figure 3C:
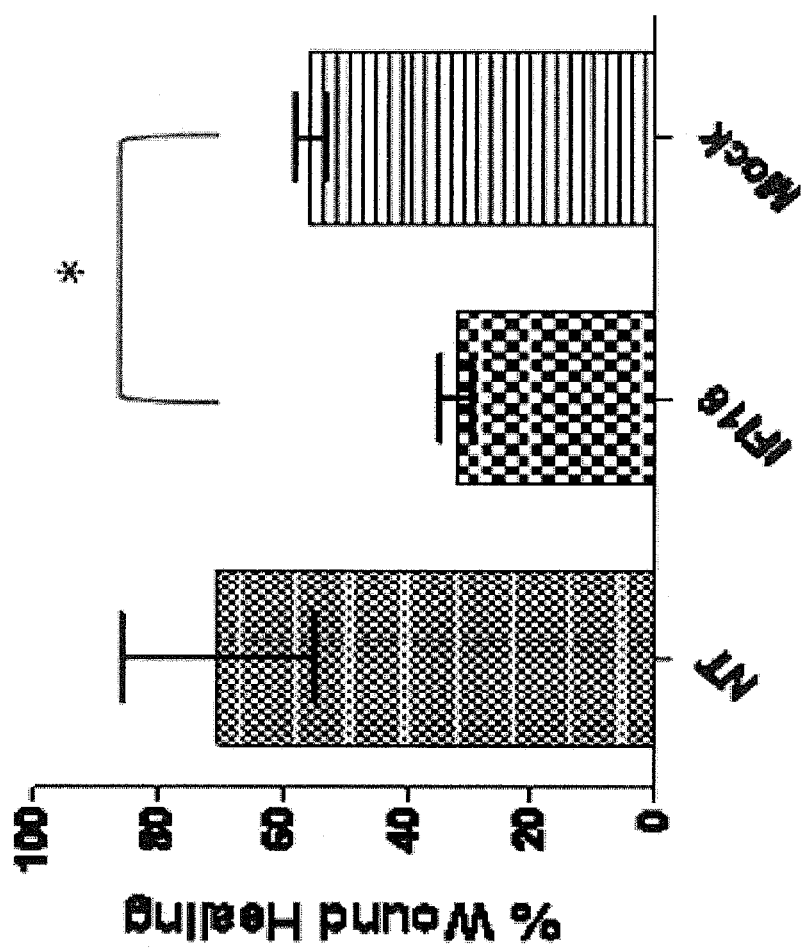

FIGS. 3b and 3c: In vitro scratch assay on human epithelial keratinocytes. FIG. 3b) Representative images of cells treated with recombinant IFI16 protein, Mock or left untreated for 48 hours; FIG. 3c) analysis of wound closure data of cells treated with recombinant IFI16 protein, Mock or left untreated for 48 hours. Values represent the mean±SEM of four independent experiments (* $p=0.0062$, Paired t test).

Primary human keratinocytes (KER) were seeded at a density of $2.5\times10^5$ in a 12 well culture plate and grown to confluence for 24 hours. Then the medium was removed and cells were washed with PBS. Three scratches (one vertical and two horizontals) were carefully created using a pipette tip to rub the confluent cell monolayer to make a cell-free area. Cells were washed twice with PBS to remove scratched debris and were photographed (t=0) using a Leica inverted microscope (FIG. 3b). Epilife complete medium, containing 10 µg/ml recombinant IFI16 protein, was then added and cells were incubated for 48 hours, when pictures of the same areas were taken (FIG. 3b). Wounded areas were measured using Microsoft Power Point, and data were graphed as % wound closure (FIG. 3c). As negative controls, cells were treated with medium containing the same volume of vehicle (Mock) or left untreated (NT).

Figure 4A:
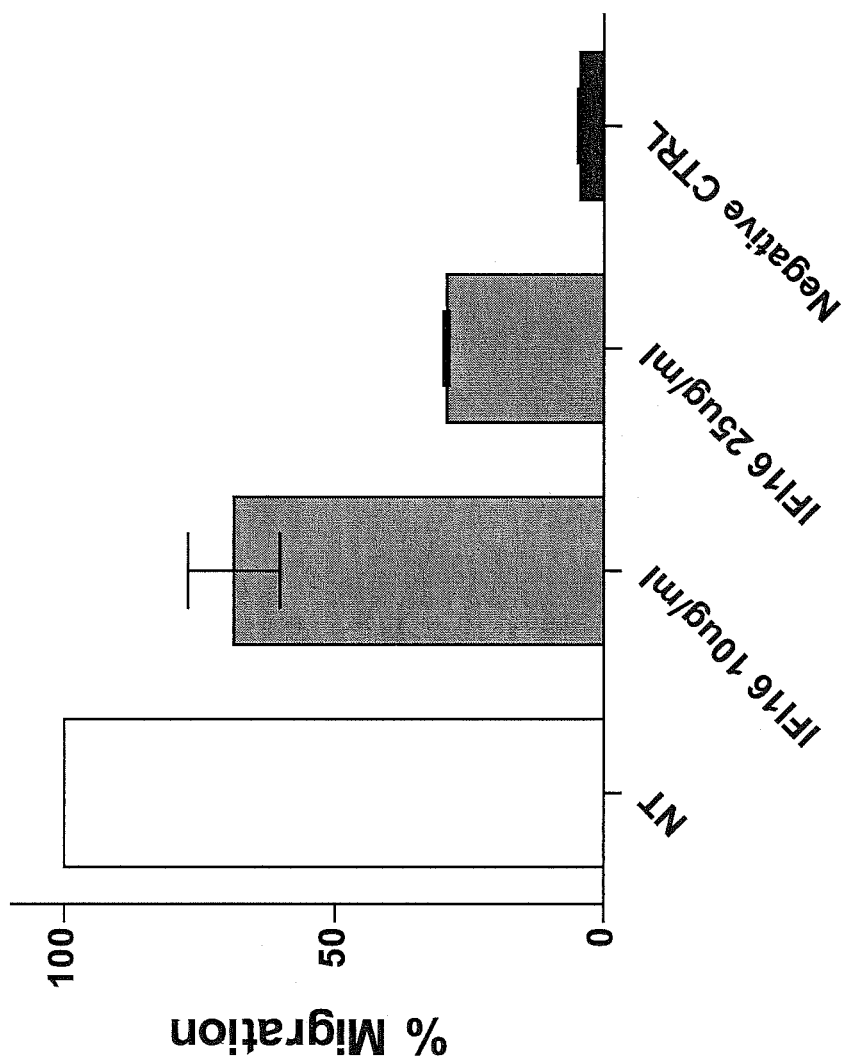

FIG. 4a: Transwell migration assay analysis of adherent human endothelial cells treated with IFI16.

Extracellular IFI16 impairs HUVEC migration. This test was carried out in 24-well transwell inserts with a 8 µm pore size (Corning) coated with a thin layer of gelatin (0.2%). HUVEC were treated with different doses (10 or 25 µg/ml) of rIFI16 or left untreated for 48 hours and then resuspended in EBM-2, 0.1% BSA. The lower compartment of Boyden chambers was filled with 600 µl EGM2 containing VEGF and bFGF as chemoattractants, 2% FBS and IFI16 (the same amounts of the upper chamber). EBM-2 without chemoattractants supplemented with 0.1% BSA was used as a negative control. HUVEC (400000 cells/200 µl) were placed in the upper compartment and, where appropriate, IFI16 was added to the medium. The chambers were incubated for 5 h at 37° C. in a humidified atmosphere containing 5% $CO_2$. After incubation, cells on the upper side of the filter were removed. The cells that had migrated to the lower side of the filter were washed twice with PBS, fixed with 2.5% glutaraldehyde for 20 min at room temperature, and stained with 0.5 ml crystal violet (0.1% in 20% methyl alcohol solution). After washes, color was developed in 10% acetic acid and read in duplicate at 540 nm on a microplate reader (Victor 3; Perkin-Elmer, Boston, Mass.).

Figure 4B:
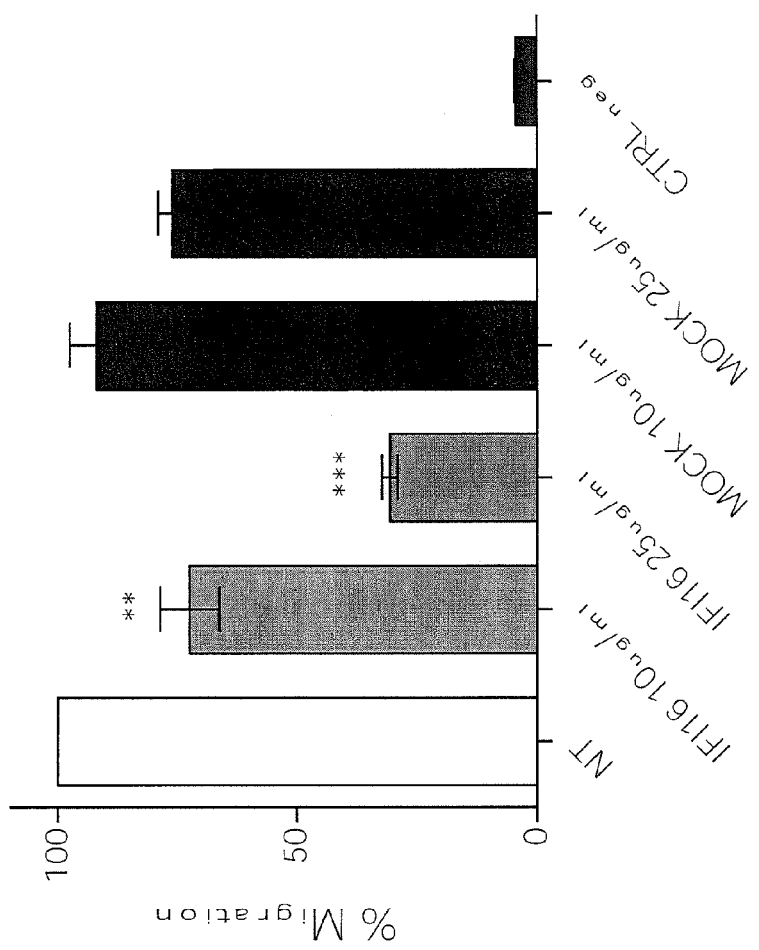

FIG. 4b: Migration analysis of HUVEC cells treated with different doses of recombinant IFI16 protein, Mock treated or left untreated for 48 hours. Values represent the mean±SEM of 3 independent experiments, and are reported as the percentage of migrated cells when compared to untreated HUVEC ( $P<0.01$, * $P<0.001$, one-way ANOVA followed by Bonferroni's Multiple Comparison Test).

24-well transwell inserts with a 8 µm pore size (Corning) were coated with a thin layer of gelatin (0.2%). HUVECs, cultured in EGM-2 with 2% FBS and pre-treated with different concentrations of IFI16 recombinant protein or Mock or untreated for 48 hours, were washed twice with PBS, trypsinized and plated into the upper chambers (400,000 cells) resuspended in 200 µl of EBM-2, 0.1% BSA plus IFI16 recombinant protein or mock (the same amounts of the 48 hours pre-treatment). The lower compartment of chambers was filled with 600 µl EGM2 containing VEGF and bFGF as chemoattractants, 2% FBS. The chambers were incubated for 5 hours at 37° C. in a humidified atmosphere containing 5% $CO_2$. After incubation, cells on the upper side of the filter were removed. The cells that had migrated to the lower side of the filter were washed twice with PBS, fixed with 2.5% glutaraldehyde for 20 min at room temperature, and stained with 0.5 ml crystal violet (0.1% in 20% methyl alcohol solution). After washes, color was developed in 10% acetic acid and read in duplicate at 540 nm on a microplate reader (Victor 3; Perkin-Elmer, Boston, Mass.).

Figure 5:
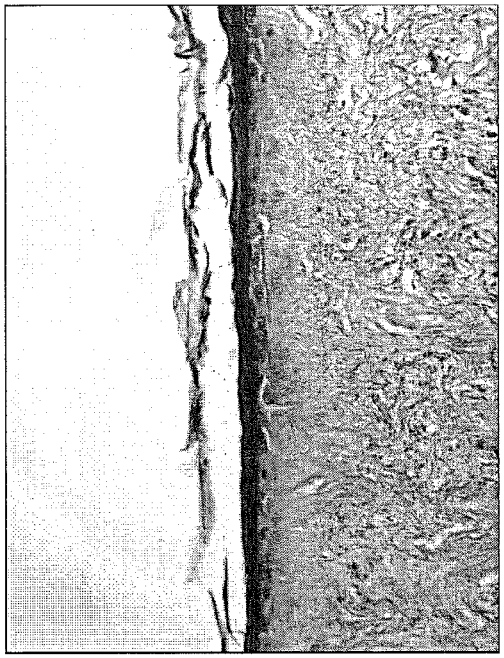
Figure 5:
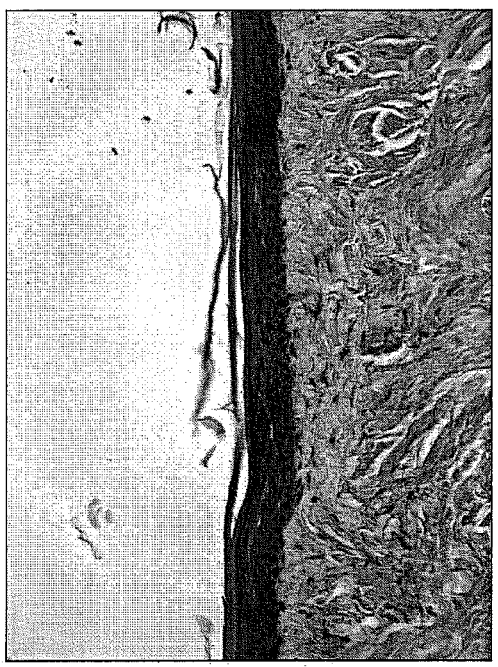

FIG. 5: Effects of IFI16 on epidermal raft cultures.

Preliminary experiments suggest that extracellular IFI16 impairs morphogenesis of epidermal raft cultures. Glycerol-preserved skin (Euro Skin Bank, Beverwijk, Holland) was washed and incubated in DPBS containing penicillin, streptomycin, gentamicin sulphate and amphotericin-B at 37° C. until the epidermis was detached from the dermis. Deepidermalized dermis was cut into 2 cm squares and placed in culture plates with the epidermal-dermal junction on the underside. Glass rings were placed on top of the dermis, and $5\times10^5$ human primary fibroblasts were plated on the dermal surface. After 24 h of incubation and orientation of the dermal equivalent with the epidermal-dermal surface on top before replacing the rings, $5\times10^5$ KER were seeded onto inserts. After 2 days of incubation, the dermis was raised to the air-liquid interface in the same orientation. Raft cultures were maintained in FAD medium [(1 part Ham's F12 and 3 parts DMEM) in the presence of 10% heat inactivated FBS (F12/DMEM/10% FBS), insulin (0.4 mg/ml), epidermal growth factor (EGF, 10 ng/ml), cholera toxin (8.4 ng/ml), hydrocortisone (0.4 µg/ml), apo-transferrin (5 µg/ml), 3,3',5'-triiodo-L-thyronine sodium salt (13 ng/ml) and ascorbic acid (50 µg/ml)] in the presence of penicillin, streptomycin and amphotericin-B solution at 37° C. in a humidified 5% $CO_2$. After one week, 10 µg/ml of IFI16 was added in the FAD medium or cultures were left untreated.

After another week, raft cultures were harvested by fixation in 10% buffered formalin, embedded in paraffin, cut into 5-µm sections, and stained with hematoxylin and eosin (H&E) for histological examination.

Figure 6A:
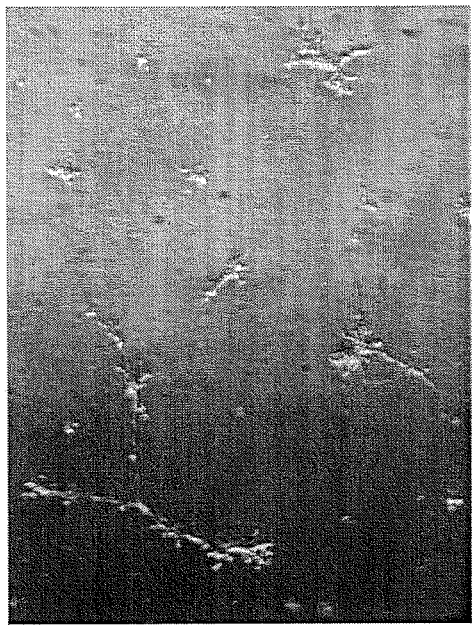
Figure 6A:
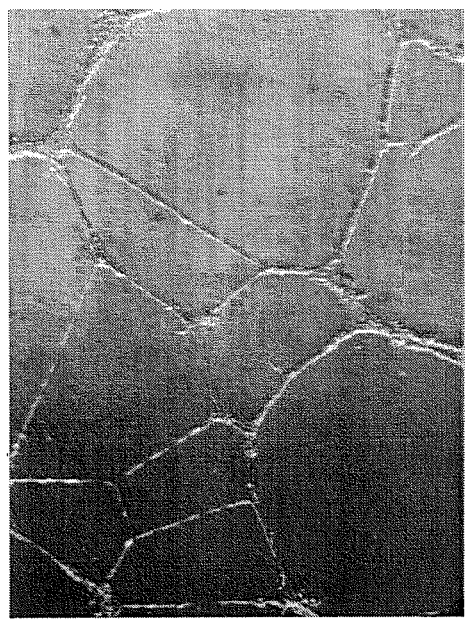

FIG. 6a: MATRIGEL™ assay analysis of adherent human endothelial cells treated with IFI16.

Tubulogenesis of primary human endothelial cells is affected by extracellular IFI16. A 24-microwell plate, pre-chilled at −20° C., was coated with 250 µl/well of MATRIGEL™ Basement Membrane (5 mg/ml; Becton and Dickinson) and then placed in an incubator at 37° C. for 30 min until solidified. $8\times10^4$ cells/(500 µl well) HUVEC in complete medium, pretreated or not with 25 µg/ml of IFI16 for 48 hours, were seeded onto the matrix and incubated at 37° C. in a 5% $CO_2$ environment. Plates were photographed at 6 h (after seeding) using a Leica inverted microscope.

FIG. 6b: Capillary-like tube formation assay (MATRIGEL™ assay) of HUVEC cells treated with recombinant IFI16 protein, Mock or left untreated for 48 hours. Representative images of three independent experiments are reported.

HUVEC cells, seeded in complete medium in a 60-mm culture dishes coated with 0.2% gelatine, were treated for 48 hours with different doses (10 or 25 µg/ml) of recombinant IFI16 protein (IFI16) (produced by Notopharm srl). As negative controls, cells were treated with the same volumes of vehicle (Mock) (produced by Notopharm srl) used for each IFI16 dose or left untreated (NT). A 24-microwell plate, pre-chilled at −20° C., was coated with 250 µl/well of MATRIGEL™ Basement Membrane (5 mg/ml; Becton and Dickinson, Milan, Italy) and then incubated at 37° C. for 30 min until solidified. HUVEC cells ($8\times10^4$ cells/500 µl per well), were seeded onto the matrix and allowed to incubate at 37° C. and 5% $CO_2$. Plates were photographed after 6 hours using a Leica inverted microscope.

Figure 7:
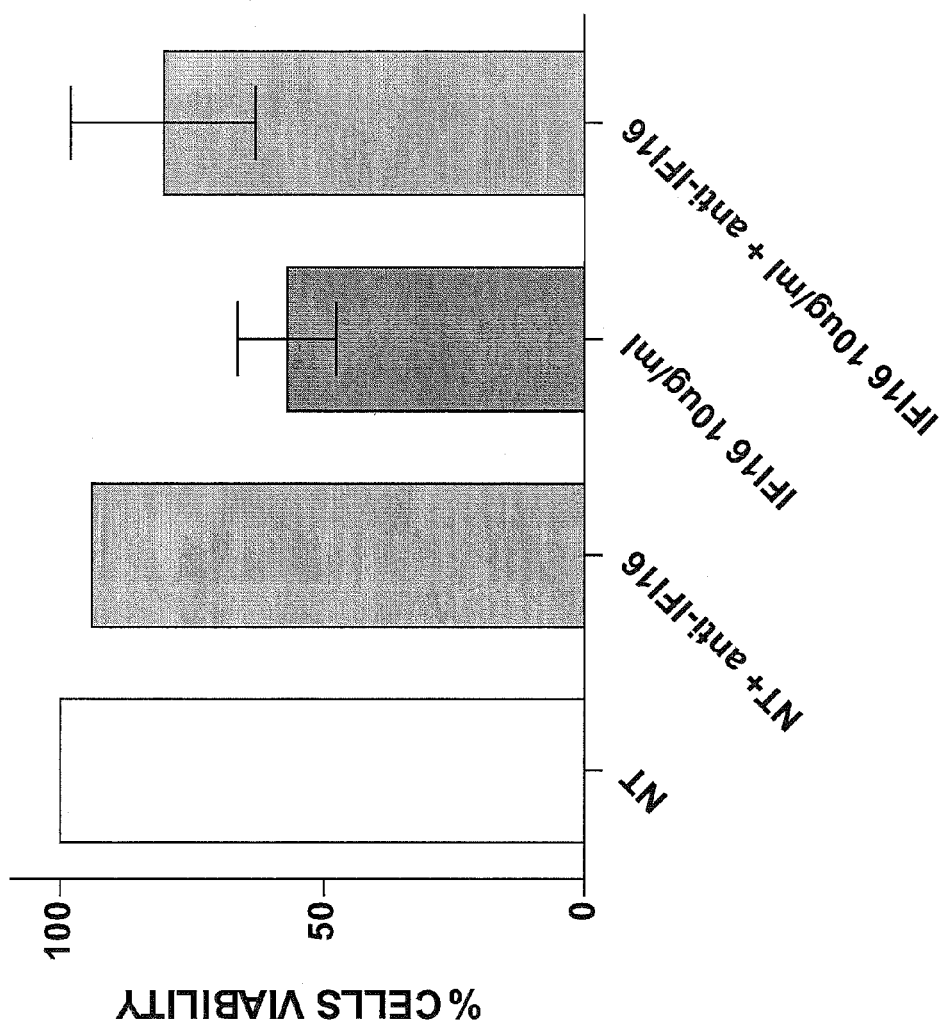
Figure 8:
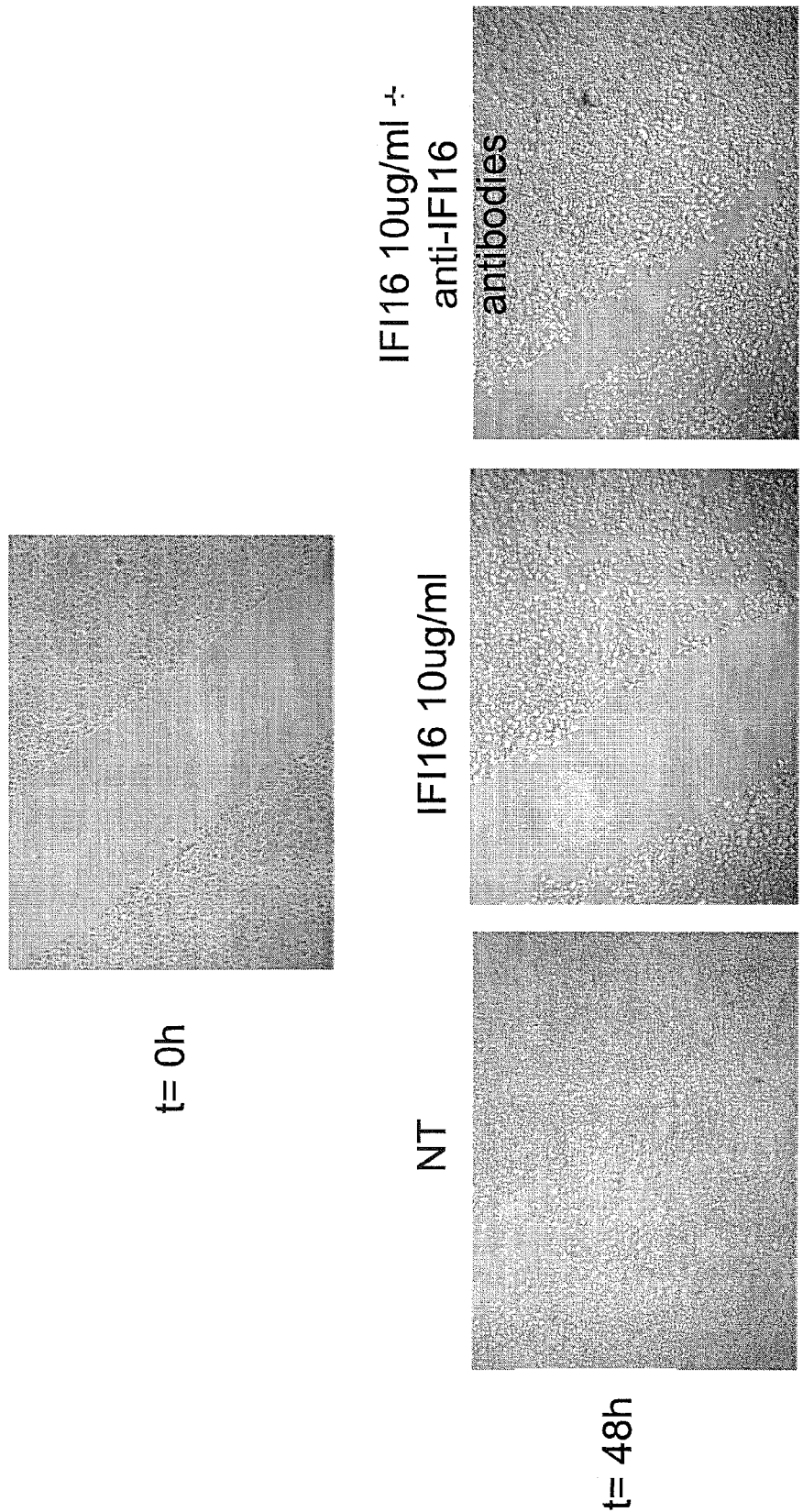

FIG. 7: Viability analysis of adherent human endothelial cells treated with IFI16 and/or anti-IFI16 antibodies.

Effects of IFI16 on the amount of viable adherent HUVEC were limited by anti-IFI16 antibodies. Primary human umbilical vein embryo cells (HUVEC) were cultured in complete endothelial growth medium (EGM-2, Clonetics, USA) containing 2% FBS. 10 µg/ml of IFI16 and equimolar amount of anti-IFI16 antibodies were pre-incubated for 1 hours at 37° C. 3000 cells were seeded in a 96 well culture plate and after 24 hours treated with IFI16, anti-IFI16 or IFI16+anti-IFI16 or left untreated. After 48 hours, the cells were treated with 3-(4,5-Dimethylthiazol-2-yl)-2,5-diphenyltetrazolium bromide (MTT) for 3 hours at 37° C. and then the medium was aspirated and the MTT crystals were dissolved with DMSO. The absorbance, proportional to the amount of viable adherent cells, was read at 570 nm.

FIG. 8: In vitro scratch assay analysis of adherent human epithelial cells treated with IFI16 and/or anti-IFI16 antibodies.

Anti-IFI16 antibodies restore the wound healing capabilities of IFI16-treated primary human keratinocyte. The cells were seeded to a density of $5\times10^5$ in a 6 well culture plate and grown to confluence for 24 hours. Then the medium was removed and cells were washed with PBS. Three artificial wounds (one vertical and two horizontal) were carefully created using a pipette tip to scratch the confluent cell monolayer to make a cell-free area. Plates were photographed using a Leica inverted microscope (0 hours). The cells were washed twice with PBS to remove scratched debris. Epilife complete medium, containing IFI16 (10 µg/ml), anti-IFI16 (equimolar amount) or IFI16+anti-IFI16 (equimolar amount) or left untreated, was then added and cells were incubated for 48 hours, when pictures of the same areas were taken.

Figure 9:
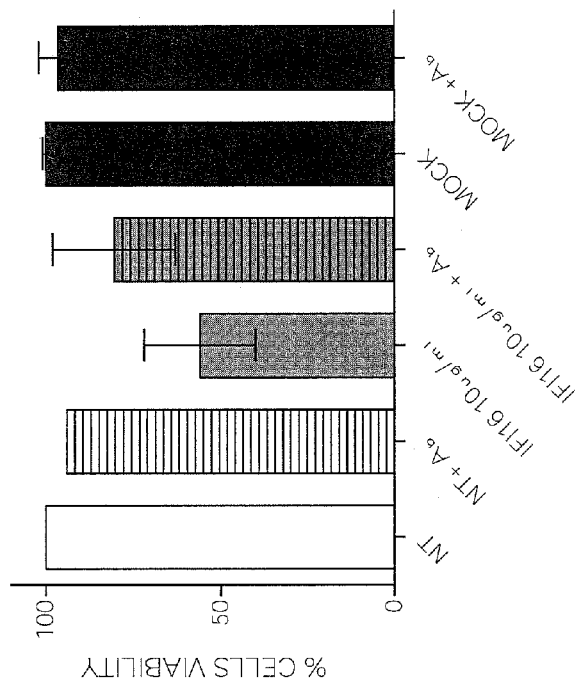

FIG. 9: Viability analysis of HUVEC cells treated with recombinant IFI16 protein (IFI16) alone or in combination with an antibody against IFI16, Mock treated or left untreated (NT) for 48 hours. Values represent the mean±SEM of 2 independent experiments.

$3\times10^3$ Human umbilical vein endothelial cells (HUVEC) cells were seeded in a 96 well culture plate and after 24 hours treated with 10 µg/ml of recombinant IFI16 protein (IFI16) (produced by Notopharm srl), which was preincubated or not with equimolar amounts of a polyclonal antibody against IFI16. As negative controls, cells were treated with the same volumes of vehicle (Mock) (produced by Notopharm srl) and/or with anti-IFI16 antibodies, or left untreated (NT). After 48 hours incubation, cells were treated with 3-(4,5-Dimethylthiazol-2-yl)-2,5-diphenyltetrazolium bromide (MTT) for 2 hours at 37° C., then the medium was discarded and the MTT crystals were dissolved with DMSO. The absorbance, proportional to the amount of viable adherent cells, was read at 570 nm with a spectrophotometer.

EXAMPLES

Example 1

Extracellular IFI16 is Found in the Sera of Patients Suffering of Autoimmune, Inflammatory and Infective Diseases The concentration of circulating IFI16 in sera was determined by means of ELISA in patients suffering from Systemic Sclerosis (SSc, n=50), Systemic Lupus Erytemathosus (SLE, n=50), Sjogren's Syndrome (SjS n=51), Rheumatoid Arthritis (RA, n=50), Anti-Phospholipid Syndrome (pAPS, n=80) and patients with Hepatitis C Virus infection (HCV, n=82) and in healthy subjects (CTRL, n=50). Extracellular IFI16 was found in concentrations significantly higher than in the control population in the sera of SSc, SLE, SjS, RA and HCV patients, with a positivity of up to 80%. (FIG. 1)

Example 2

Extracellular IFI16 Exerts Biological Activities on Primary Human Cells 2.1 Extracellular IFI16 Affects the Amount of Viable Adherent Human Epithelial and Endothelial Cells Exogenous IFI16 administration lowers the amount of viable adherent cells, as measured by MTT assay, when compared to untreated control cells. Indeed, a dose-dependent decrease (up to 50%) of viable adherent primary human epithelial cells (KER) was observed when cells were treated with recombinant IFI16, added in culture media at different concentration for 48 hours (FIG. 2a, Panel A). An even more consistent reduction was observed in human primary endothelial cells (HUVEC) treated with extracellular IFI16 (FIG. 2a, Panel B). In contrast, addition to culture media of a control vehicle did not significantly affect cell viability, with only a slight reduction observed when a volume of vehicle corresponding to that used for the highest IFI16 dose, possibly due to the dilution of media growth factors.

Further experiments confirmed that exogenous IFI16 administration lowers the amount of viable adherent cells, as measured by MTT assay, when compared to Mock-treated cells. Indeed, a decrease (19%, for both IFI16 concentrations) of viable adherent primary human epithelial cells (keratinocytes) was observed (FIG. 2b).

Still further experiments have been conducted to show that the administration of exogenous IFI16 lowers the amount of viable adherent cells, as measured by MTT assay, when compared to Mock-treated cells. The amount of viable adherent HUVEC after IFI16 or mock treatments were analyzed by the MTT assay. Detached cells were washed away prior to MTT assay analysis. A significative decrease (up to 45%) of viable adherent HUVEC cells was observed, when treated with extracellular IFI16 (FIG. 2c).

2.2 Extracellular IFI16 Impairs Migration of Human Primary Endothelial and Epithelial Cells To evaluate the involvement of extracellular IFI16 on migration of human epithelial cells, human keratinocytes (KER) were subject to an in vitro scratch assays, which is used to mimic cell migration during wound healing in vivo (Liang C C et al., Nat. Protoc. 2007). As observed in FIG. 3a, addition of extracellular IFI16 to culture media resulted in a severely decrease of wound repair compared with control cells. Indeed, while the untreated cells almost completely closed the wound 48 hours after the scratch was made, only few IFI16 treated cells were able to migrate in the scratched area.

Further data were obtained to evaluate the involvement of extracellular IFI16 on human epithelial cells migration, whereby keratinocytes were subjected to an in vitro scratch assay, which is used to mimic cell migration during wound healing (Liang C C et al., Nat. Protoc. 2007). Addition of extracellular IFI16 to culture media resulted in a significant decrease (mean=24%) in the wound repair ability when compared with mock-treated cells (FIGS. 3b and 3c).

The migration rate of HUVECs in presence or absence of IFI16 was analyzed by a transwell migration assay. Endothelial cells, pretreated or not with extracellular IFI16, were plated in the upper section of a modified Boyden chamber and then left to migrate across the membrane, containing pores large enough (8 µm) to allow cell passage, for 5 hours. As shown in FIG. 4a, a significantly less HUVECs were able to cross the membrane when treated with extracellular IFI16, which acted in a dose-dependent manner.

These data were confirmed by further experiments showing that exogenous IFI16 administration decreases the migration of HUVEC cells in response to chemotactic factors. The Transwell migration assay is a commonly used test to study the migratory response of endothelial cells to angiogenic inducers or inhibitors. As shown in FIG. 4b, exogenous IFI16 administration reduces the ability of HUVEC cells to respond to the chemotactic factors (VEGF and bFGF) when compared with mock-treated or untreated cells.

2.3 Extracellular IFI16 Impairs Morphogenesis of Epidermal Raft Cultures

To evaluate the potential effects of extracellular IFI16 on skin morphogenesis, primary human keratinocytes were plated on deepidermalized human derma (obtained from preserved skin) and allowed to differentiate at the air-liquid interface for 2 weeks. When IFI16 was added to the culture media of the raft cultures for 1 week, the epithelial morphogenesis was severely affected, resulting in a thinner epithelium when compared to untreated cultures (see representative pictures in FIG. 5). The pluristratification, as consequence of keratinocytes differentiation, was impaired and the layers were not distinguishable in IFI16 treated skin equivalents, as demonstrated by the H/E staining in FIG. 5. These data are results obtained by preliminary tests.

2.4 Tubulogenesis of Primary Human Endothelial Cells is Affected by Extracellular IFI16

Tubulogenesis (morphogenesis of branched tubular structures), is an essential process in vascular development. BD MATRIGEL™ Basement Membrane Matrix is a gelatinous mixture that resembles the complex extracellular environment found in many tissues. MATRIGEL™ is used for in vitro angiogenesis assays using primary endothelial cells: when endothelial cells are plated on MATRIGEL™, the cells stop proliferating, display high motility and cell-cell communication. As expected, when plated on a MATRIGEL™ matrix, untreated primary HUVEC formed capillary-like structures within 6 hours (FIG. 6a, left panel). In contrast, when cells where pretreated by adding IFI16 to the culture media for 48 hours before they were seeded in MATRIGEL™, their ability to form tubules was severely affected, resulting in shorter tubular structures with few branches (FIG. 6a, right panel). Extracellular IFI16 thus play a role in the inhibition of tubulogenesis by primary human endothelial cells.

Further experiments have been conducted confirming that administration of extracellular IFI16 decreases the angiogenic activity on HUVEC cells. MATRIGEL™ assay is an in vitro assay that mimics human angiogenesis in which native human umbilical vein-derived endothelial cells are suspended in a liquid laminin/collagen gel (MATRIGEL™). As shown in FIG. 6b, exogenous IFI16 administration inhibits angiogenesis of HUVEC cells. Indeed, addition of extracellular IFI16 to culture media resulted in a significant decrease of ability of endothelial cells (HUVEC) to form microtubules in MATRIGEL™ when compared with mock-treated or untreated cells.

Example 3

Extracellular Ifi16 Effects can be Inhibited by Anti-Ifi16 Antibodies 3.1 Effects of IFI16 on the Amount of Viable Adherent HUVEC are Limited by Anti-IFI16 Antibodies To evaluate whether the biological effects of extracellular IFI16 could be inhibited, equimolar amounts of antibodies directed against IFI16 (anti-IFI16) were added to IFI16 solution before its addition to culture media. In cultures treated with anti-IFI16+IFI16 only a slight reduction of adherent cells viability was observed, in contrast to the almost 50% reduction of cells treated with extracellular IFI16 alone (FIG. 7). As expected, anti-IFI16 administration alone did not affect cell viability.

3.2 Anti IFI16 Antibodies Restore the Wound Healing Capabilities of IFI16-Treated Primary Human Keratinocytes Preincubation of IFI16 with an equimolar amounts of anti-IFI16 antibodies, before the addition to culture media of scratched keratinocytes, resulted in a significant restoration of their ability to migrate in the scratched area. Indeed, as shown in FIG. 8, the wound closure was significantly enhanced when cell were treated with anti-IFI16+IFI16 compared to cells treated with IFI16 alone. Thus, anti-IFI16 antibodies act as inhibitors of extracellular IFI16 activities.

3.3 Effect of Anti-IFI16 Antibodies on IFI16-Induced Cyclotoxicity

To evaluate whether the biological effects of extracellular IFI16 could be inhibited, equimolar amounts of antibodies directed against IFI16 ($A_b$) were added to IFI16 solution before its addition to culture media. In cultures treated with $A_b$+IFI16 only a slight reduction of adherent cells viability was observed, in contrast to the almost 50% reduction of cells treated with extracellular IFI16 alone (FIG. 9). As expected, anti-IFI16 administration alone did not affect cell viability. Anti-IFI16 antibodies can thus inhibit the biological activities of extracellular IFI16.

REFERENCES

1. Bekisz, J., Schmeisser, H., Hernandez, J., Goldman, N. D., and Zoon, K. C. (2004) *Growth Factors* 22, 243-251.
2. Parmar, S., and Platanias, L. C. (2005) *Cancer Treat. Res.* 126, 45-68.
3. Kong, J. S., Teuber, S. S., and Gershwin, M. E. (2006) *Autoimmun. Rev.* 5, 471-485.
4. Asefa, B., Klarman, K. D., Copeland, N. G., Gilbert, D. J., Jenkins, N. A., and Keller, J. R. (2004) *Blood Cells, Mol. & Dis.* 32, 155-167.
5. Landolfo, S., Gariglio, M., Gribaudo, G., Lembo, D. (1998) *Biochimie* 80, 721-728.
6. Ludlow, L. E. A., Johnstone, R. W., Clarke, C. J. P. (2005) *Exp. Cell Res.* 308, 1-17.
7. Inohara, N., and Nunez, G. (2003) *Nat. Rev. Immunol.* 3, 371-382.
8. Tschopp, J., Martinon, F., and Burns, K. (2003) *Nat. Rev. Mol. Cell. Biol.* 4, 95-104.
9. Aglipay, J. A., Lee, S. W., Okada, S., Fujiuchi, N., Ohtsuka, T., Kwak, J. C., Wang, Y., Johnstone, R. W., Deng, C., Qin, J., and Ouchi, T. (2003) *Oncogene* 22, 8931-8938.
10. Albrecht, M., Choubey, D., and Lengauer, T. (2005) *Biochem. Biophys. Res. Com.* 327, 679-687.
11. Gugliesi, F., Mondini, M., Ravera, R., Robotti, A., De Andrea, M., Gribaudo, G., Gariglio, M., and Landolfo, S. (2005) *J. Leukoc. Biol.* 77, 820-829.
12. Mondini, M., Vidali, M., Airò, P., De Andrea, M., Riboldi, P. S., Meroni, P. L., Gariglio, M., and Landolfo, S. (2007) *Ann N Y Acad Sci.* 1110, 47-56
13. Gariglio, M., Azzimonti, B., Pagano, M., Palestro, G., De Andrea, M., Valente, G., Voglino, G., Navino, L., and Landolfo, S. (2002) *J. Interferon Cytokine Res.* 22, 815-821.
14. Wei, W., Clarke, C. J., Somers, G. R., Gresswell, K. S., Loveland, K. A., Trapani, J. A., and Johnstone, R. W. (2003) *Histochem Cell Biol* 119, 45-54.
15. Asefa B, Klarmann K D, Copeland N G, Gilbert D J, Jenkins N A, Keller J R. (2004) *Blood Cells Mol Dis;* 32:155-67.
16. Caposio, P., Gugliesi, F., Zannetti, C., Sponza, S., Mondini, M., Medico, E., Hiscott, J., Young, H. A., Gribaudo, G., Gariglio, M., Landolfo S. (2007) *Biol Chem;* 282, 33515-29.
17. Mondini, M., Vidali, M., De Andrea, M., Azzimanti, B., Airò, P., Riboldi, P. S., Meroni, P. L., Albano, E., Shoenfeld, Y., Gariglio, M., and Landolfo, S. (2006) *Arthritis Rheum* 54, 3939-3944.

The invention claimed is:

1. A method of treating a subject suffering from at least one autoimmune disease selected from the group consisting of Systemic Sclerosis (SSc), Systemic Lupus Erythematosus (SLE), Sjogren's Syndrome (SjS) and rheumatoid arthritis, comprising administering to said subject in need thereof a pharmaceutically effective amount of an antibody specific for extracellular IFI16.

* * * * *